United States Patent [19]
Aono et al.

[11] Patent Number: 4,732,846
[45] Date of Patent: Mar. 22, 1988

[54] HEAT-DEVELOPABLE LIGHT-SENSITIVE MATERIAL

[75] Inventors: Toshiaki Aono; Masatoshi Kato; Hiroshi Hara, all of Kanagawa, Japan

[73] Assignee: Fuji Photo Film Co., Ltd., Kanagawa, Japan

[21] Appl. No.: 857,285

[22] Filed: Apr. 30, 1986

[30] Foreign Application Priority Data

Apr. 30, 1985 [JP] Japan .................................. 60-91258

[51] Int. Cl.⁴ .......................... G03C 1/40; G03C 5/54
[52] U.S. Cl. .................................... 430/619; 430/203; 430/559; 430/351; 430/353; 430/612; 430/620
[58] Field of Search ............... 430/620, 619, 612, 203, 430/559, 351, 353

[56] References Cited

U.S. PATENT DOCUMENTS

| | | | |
|---|---|---|---|
| 3,893,860 | 7/1975 | Sutton et al. | 430/619 |
| 4,220,709 | 9/1980 | de Mauriac | 430/620 |
| 4,258,129 | 3/1981 | Ikenoue et al. | 430/620 |
| 4,603,103 | 7/1986 | Hirai et al. | 430/617 |

*Primary Examiner*—Won H. Louie
*Attorney, Agent, or Firm*—Sughrue, Mion, Zinn, Macpeak and Seas

[57] ABSTRACT

A heat-developable light-sensitive material is described, comprising a support having provided thereon at least
(a) a binder;
(b) a light-sensitive silver halide;
(c) at least one silver salt of a compound represented by formula (I) or (II)

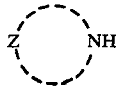

(I)

wherein Z represents a non-metallic atomic group forming a heterocyclic ring together with the nitrogen atom,

A—C≡C—H (II)

wherein A represents a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group;
(d) a silver salt of a compound represented by formula (III)

B—S—H (III)

wherein B represents a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group; and
(e) a reducing agent.

The material exhibits stable developability despite variations in development temperature or time, and provides an image having high maximum density and low minimum density.

17 Claims, No Drawings

HEAT-DEVELOPABLE LIGHT-SENSITIVE MATERIAL

FIELD OF THE INVENTION

This invention relates to a novel heat-developable light-sensitive material which provides an image, particularly a dye image, upon heating.

BACKGROUND OF THE INVENTION

Photography using silver halides has long been widely used because of excellence in photographic characteristics, such as sensitivity and gradation control as compared with other photographic techniques, such as electrophotography and diazo processes. For simpler and faster image formation with silver halide photographic materials, conventional wet processes using a developing solution, etc., have recently tended to be replaced by dry processes using heating, etc.

Many processes for dye (color) image formation have hitherto been proposed. For example, processes for forming a dye image by coupling between an oxidation product of a developing agent and a coupler include use of p-phenylenediamine reducing agents and phenolic or active methylene couplers as described in U.S. Pat. No. 3,531,286; use of p-aminophenol reducing agents as disclosed in U.S. Pat. No. 3,761,270; use of sulfonamidophenol reducing agents as described in Belgian Pat. No. 802,519 and *Research Disclosure,* Vol. 137 (September, 1975), pp. 31–32; and use of sulfonamidophenol reducing agents and 4-equivalent couplers as described in U.S. Pat. No. 4,021,240.

*Research Disclosure,* RD No. 16966 (May, 1978), pp. 54–58 describes a process comprising forming a silver salt of a dye having introduced therein a nitrogen-containing heterocyclic ring and causing the silver salt to release the dye upon heat development.

For positive image formation by the silver dye bleach process, useful dyes and processes of bleaching are described, e.g., in *Research Disclosure,* RD No. 14433 (April, 1976), pp. 30–32, ibid., RD No. 15227 (December, 1976), pp. 14–15, U.S. Pat. No. 4,235,957, etc.

Further, dye image formation using leuco dyes is described, e.g., in U.S. Pat. Nos. 3,985,565 and 4,022,617.

However, the above-described various processes generally require a relatively long time for development and produce images of high fog and low density.

In order to eliminate such disadvantages, an image formation process using silver halide, in which a mobile dye is imagewise formed and then transferred to a dye-fixing layer, has been proposed, as disclosed in Japanese Patent Application (OPI) Nos. 58543/83 (U.S. Pat. No. 4,500,626), 79247/83 (U.S. Pat. No. 4,483,914), 149046/83, and 149047/83 (the term "OPI" used herein means "published unexamined application").

The conventional heat-developable light-sensitive materials have disadvantages in that the development speed is not sufficient and that the maximum density of a resulting image is not sufficiently high. Further, attempts to accelerate development or to increase the maximum density by altering development conditions, such as a heating temperature, a heating time, etc., result in an increase of the minimum density, i.e., fog, even though an improved maximum density may be attained. In addition, satisfactory images cannot be stably obtained unless the development conditions are maintained constant. In other words, developability is unstable with respect to variation from the optimum development conditions.

SUMMARY OF THE INVENTION

Accordingly, an object of the present invention is to provide a compound which accelerates development while suppressing fog and a heat-developable light-sensitive material containing such a compound.

Another object of this invention is to provide a heat-developable light-sensitive material whose developability undergoes little change with respect to variation in temperature or time from optimum development conditions, that is, a heat-developable light-sensitive material having stable developability.

These objects can be accomplished by a heat-developable light-sensitive material comprising a support having provided thereon at least (a) a binder;

(b) a light-sensitive silver halide;

(c) at least one silver salt of a compound represented by formula (I) or (II)

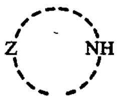

(I)

wherein Z represents a non-metallic atomic group forming a heterocyclic ring together with the nitrogen atom,

A—C≡C—H (II)

wherein A represents a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group;

(d) a silver salt of a compound represented by formula (III)

B—S—H (III)

wherein B represents a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group; and (e) a reducing agent.

DETAILED DESCRIPTION OF THE INVENTION

In the above-described formula (I), the heterocyclic ring formed by Z is preferably a 5- to 7-membered heterocyclic ring, and may have a condensed ring and may further contain a hetero atom other than the nitrogen atom.

Among the silver salts of the compounds represented by formula (I), silver salts of compounds represented by formulae (I-1) to (I-9) are preferred.

(I-1)

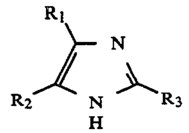

(I-2)

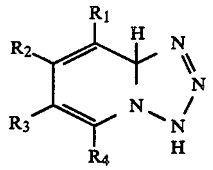

(I-3)

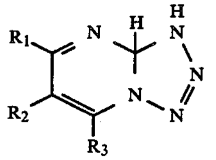

(I-4)

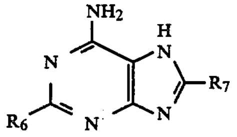

(I-5)

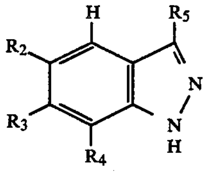

(I-6)

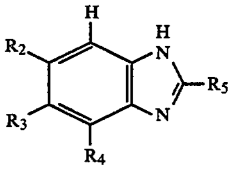

(I-7)

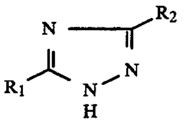

(I-8)

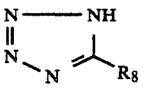

(I-9)

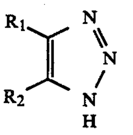

wherein $R_1$, $R_2$, $R_3$, and $R_4$ each represents a hydrogen atom, an alkyl group (preferably having from 1 to 22 carbon atoms), an aralkyl group (e.g., a benzyl group, a phenylethyl group, a tolubenzyl group, a naphthylmethyl group, etc.), an alkenyl group (preferably having from 1 to 22 carbon atoms), an alkoxy group (preferably having from 1 to 22 carbon atoms), an aryl group (preferably a substituted or unsubstituted phenyl group), —NRR′, —COOR″, —CONRR′, —$NHSO_2R$, —$SO_2NRR'$, —$NO_2$, a halogen atom, —CN, or —OH, wherein R and R′ each represents a hydrogen atom, an alkyl group (preferably having from 1 to 22 carbon atoms), an aryl group (preferably a substituted or unsubstituted phenyl group), or an aralkyl group (preferably a benzyl group, a phenylethyl group, a tolubenzyl group, a naphthylmethyl group, etc.); and R″ represents an alkyl group (preferably having from 1 to 22 carbon atoms), an aryl group (preferably a substituted or unsubstituted phenyl group), or an aralkyl group (preferably a benzyl group, a phenylethyl group, a tolubenzyl group, a naphthylmethyl group); or $R_1$ and $R_2$ in formula (I-9) may be taken together to form an aliphatic ring or an aromatic ring; $R_5$ represents a hydrogen atom, an alkyl group having from 1 to 5 carbon atoms, or —S—R‴, wherein R‴ represents a hydrogen atom, an alkyl group, an aryl group, or an aralkyl group; $R_6$ represents a hydrogen atom or an alkyl group; $R_7$ represents a hydrogen atom, an alkyl group, or an aryl group; and $R_8$ represents an alkyl group, an aryl group, a benzyl group, or a pyridyl group.

Of the compounds represented by formulae (I-1) to (I-9), silver salts of the compounds of formula (I-9) are more preferred, with the most preferred being silver salts of the compounds represented by formula (I-10)

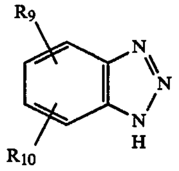

(I-10)

wherein $R_9$ and $R_{10}$ have the same meanings as $R_1$ and $R_2$.

The compounds represented by formula (II), which constitute silver salts that can be used together with or in place of the silver salts of the compounds of formula (I) as the component (b), are described below.

In formula (II), A represents a substituent selected from a substituted or unsubstituted straight chain or branched alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, and a substituted or unsubstituted heterocyclic group.

Examples of the alkyl group include a butyl group, an isobutyl group, a heptyl group, an octyl group, a dodecyl group, etc., and the substituents therefor include an alkoxy group (e.g., a methoxy group), a hydroxyl group, a cyano group, a halogen atom, a sulfonamido group, etc.

Examples of the cycloalkyl group include a cyclopentyl group, a cyclohexyl group, a decahydronaphthyl group, etc. Examples of the alkenyl group include a propenyl group, an isopropenyl group, a styryl group, etc. Examples of the alkynyl group include an ethynyl group, a phenylethynyl group, etc.

The aryl group includes a phenyl group and a naphthyl group, which may be substituted with one or more substituents. The substituents for the substituted aryl group include an alkyl group (e.g., a methyl group, a dodecyl group, etc.), a cyano group, a nitro group, an amino group, an acylamino group, a sulfonamido group (inclusive of aliphatic, aromatic, and heterocyclic groups), an alkoxy group, an aryloxy group, an alkoxycarbonyl group, a ureido group, a carbamoyl group, an acyloxy group, a heterocyclic group (preferably a 5- or 6-membered ring, with a nitrogen-containing heterocyclic ring being more preferred), an alkylsulfonyl group, a carboxyl group, a sulfo group, a sulfamoyl group, a halogen atom (e.g., fluorine, bromine, chlorine, and iodine atoms), etc. These substituents may further be substituted. Further, two or more of these substituents may be present at the same time.

Examples of the aralkyl group include a benzyl group and a phenethyl group.

The heterocyclic group preferably includes a 5- or 6-membered ring containing at least one of nitrogen, oxygen, and sulfur atoms as a hetero atom, and may be a monocyclic ring or a condensed ring thereof. Examples include a furan ring residue, a thiophene ring residue, a pyridine ring residue, a quinoline ring residue, a thiazole ring residue, a benzothiazole ring residue, etc.

Of the compounds represented by formula (III), those wherein A is a phenyl group or a substituted phenyl group are preferred.

Specific examples of compounds of formulae (I) and (II) are shown below.

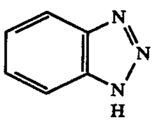
(c-1)

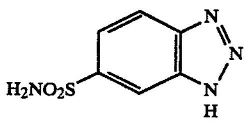
(c-2)

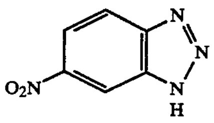
(c-3)

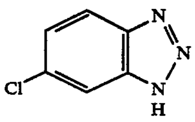
(c-4)

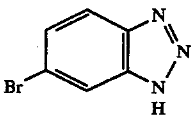
(c-5)

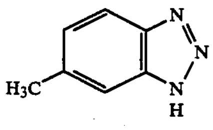
(c-6)

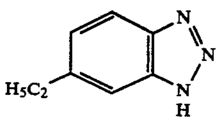
(c-7)

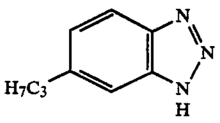
(c-8)

-continued

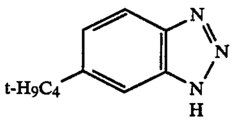
(c-9)

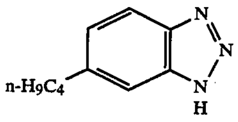
(c-10)

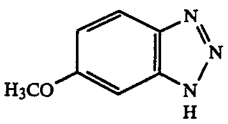
(c-11)

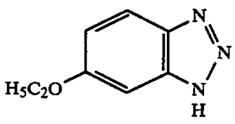
(c-12)

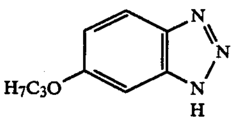
(c-13)

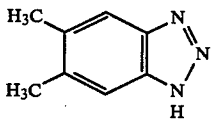
(c-14)

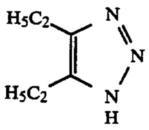
(c-15)

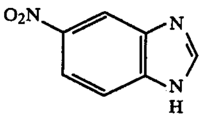
(c-16)

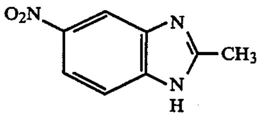
(c-17)

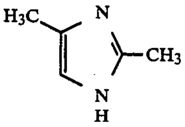
(c-18)

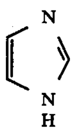
(c-19)

-continued
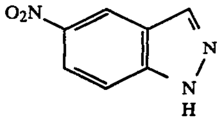
(c-20)
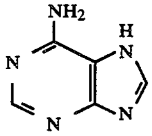
(c-21)
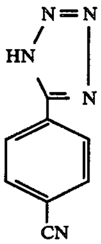
(c-22)
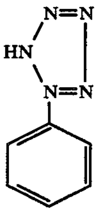
(c-23)
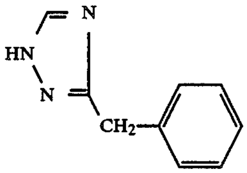
(c-24)
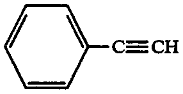
(c-25)
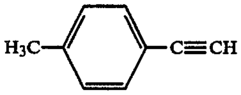
(c-26)
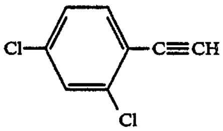
(c-27)
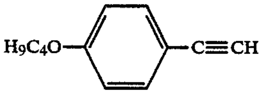
(c-28)
-continued
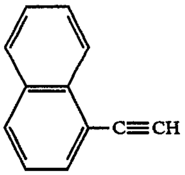
(c-29)
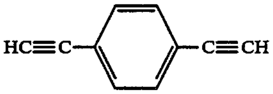
(c-30)
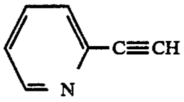
(c-31)
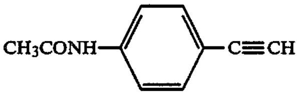
(c-32)
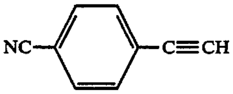
(c-33)
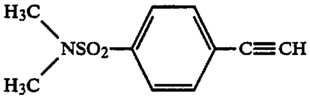
(c-34)
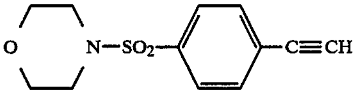
(c-35)
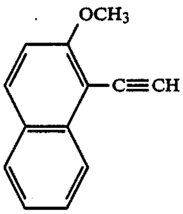
(c-36)
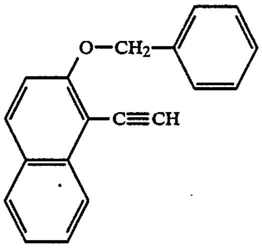
(c-37)
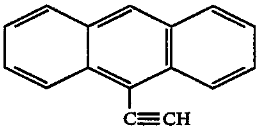
(c-38)

-continued

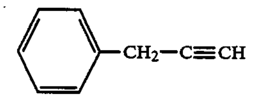
(c-39)

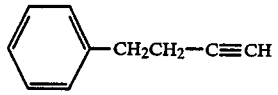
(c-40)

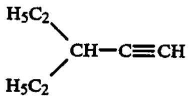
(c-41)

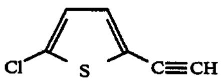
(c-42)

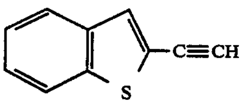
(c-43)

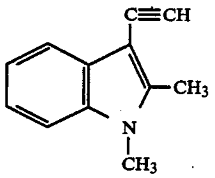
(c-44)

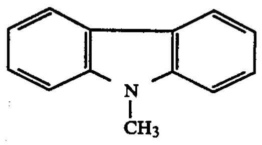
(c-45)

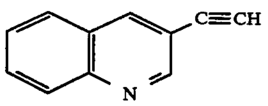
(c-46)

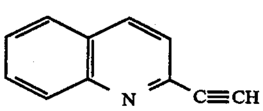
(c-47)

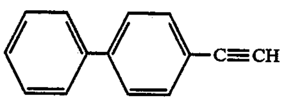
(c-48)

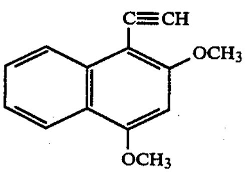
(c-49)

-continued

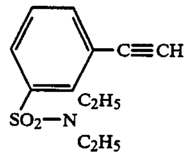
(c-50)

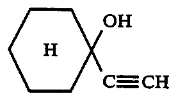
(c-60)

The component (d) that can be used together with the aforesaid component (c) as the organic silver salt is described below. The component (d) is a silver salt of a compound represented by formula (III)

B—S—H (III)

wherein B is as defined above.

Specific substituents as represented by B can be selected from the corresponding examples given for A of formula (II).

Preferred silver salts of the compounds represented by formula (III) are silver salts of compounds represented by formula (III-1)

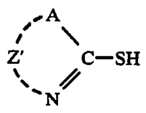
(III-1)

wherein Q represents an oxygen atom, a sulfur atom, a nitrogen atom, or —$NR_n$—, wherein $R_n$ represents a hydrogen atom, a substituted or unsubstituted alkyl group (preferably having from 1 to 22 carbon atoms), a substituted or unsubstituted cycloalkyl group (e.g., a cyclohexyl group), a substituted or unsubstituted alkenyl group (preferably having from 1 to 18 carbon atoms), a substituted or unsubstituted aryl group (preferably a substituted or unsubstituted phenyl group), or a substituted or unsubstituted aralkyl group (preferably a benzyl group, a phenylethyl group, a tolubenzyl group, or a naphthylmethyl group); and Z' represents an atomic group forming a 5- or 6-membered heterocyclic ring together with —Q—C═N—, wherein the heterocyclic ring may have a condensed ring.

Of the silver salts of the compounds represented by formula (III-1), silver salts of compounds represented by formula (III-2) are more preferred

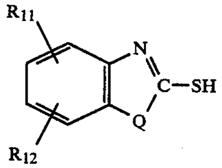
(III-2)

wherein $R_{11}$ and $R_{12}$ have the same meanings as $R_1$ and $R_2$; and Q has the same meaning as defined in formula (III-1), and is preferably —NH—.

Specific examples of the compounds of formula (III) are shown below.

(d-1)
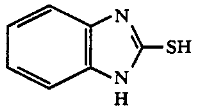
(d-2)
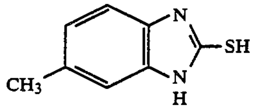
(d-3)
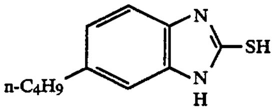
(d-4)
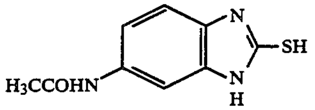
(d-5)
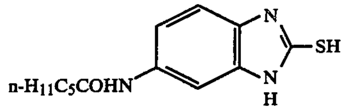
(d-6)
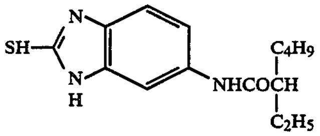
(d-7)
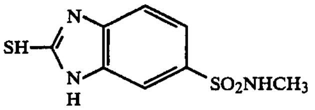
(d-8)
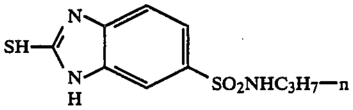
(d-9)
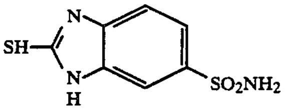
(d-10)
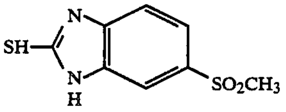
(d-11)
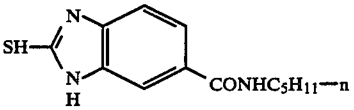
(d-12)
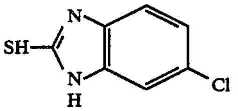
(d-13)
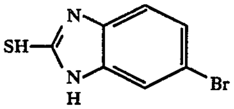
(d-14)
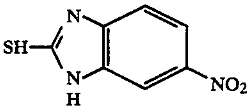
(d-15)
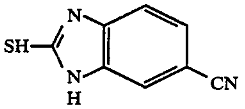
(d-16)
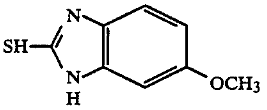
(d-17)
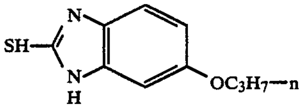
(d-18)
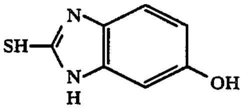
(d-19)
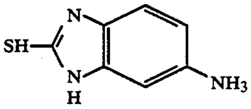
(d-20)
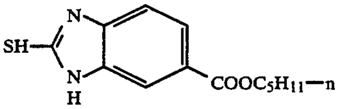
(d-21)
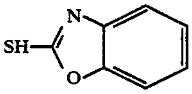
(d-22)
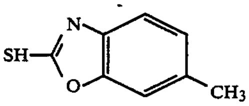
(d-23)
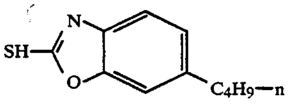
(d-24)
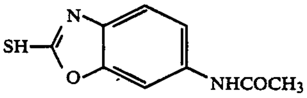

-continued
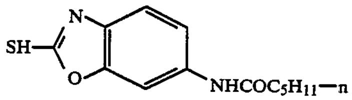
(d-25)
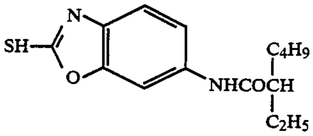
(d-26)
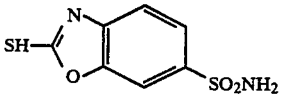
(d-27)
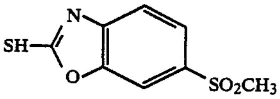
(d-28)
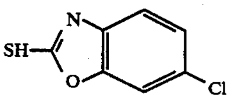
(d-29)
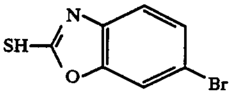
(d-30)
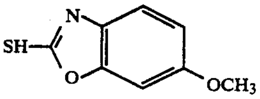
(d-31)
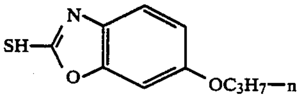
(d-32)
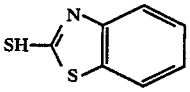
(d-33)
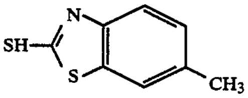
(d-34)
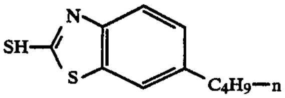
(d-35)
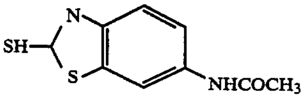
(d-36)
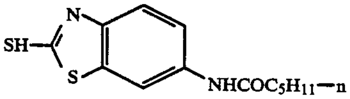
(d-37)
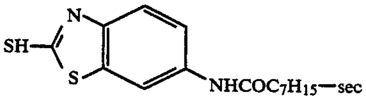
(d-38)
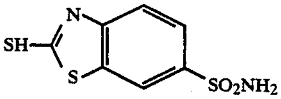
(d-39)
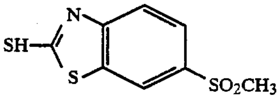
(d-40)
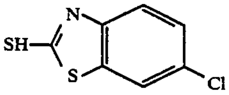
(d-41)
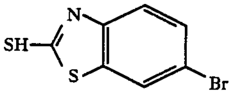
(d-42)
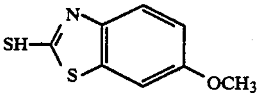
(d-43)
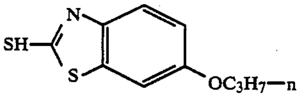
(d-44)
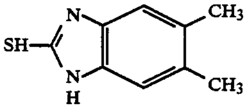
(d-45)
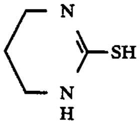
(d-46)
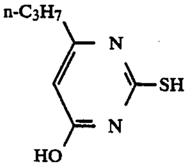
(d-47)
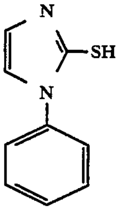
(d-48)

-continued
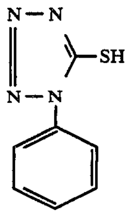
(d-49)
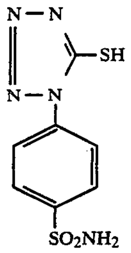
(d-50)
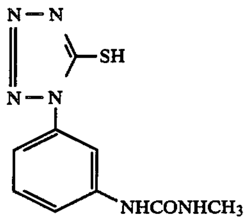
(d-51)
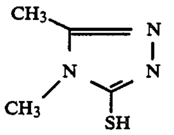
(d-52)
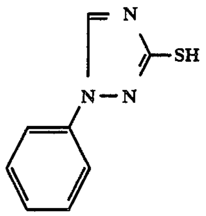
(d-53)
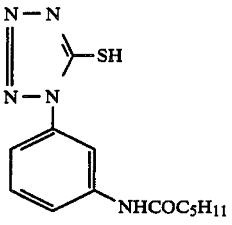
(d-54)
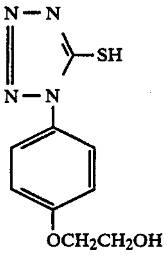
(d-55)
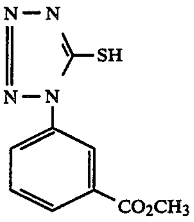
(d-56)
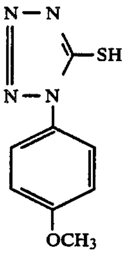
(d-57)
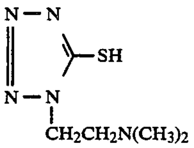
(d-58)
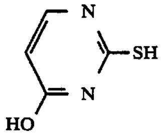
(d-59)
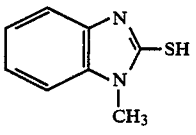
(d-60)
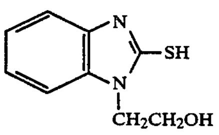
(d-61)
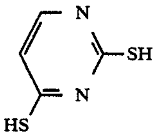
(d-62)

-continued
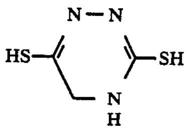
(d-63)
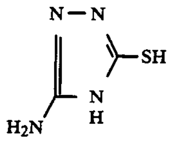
(d-64)
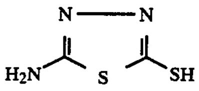
(d-65)
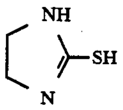
(d-66)
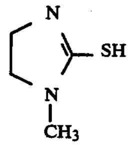
(d-67)
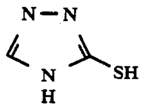
(d-68)
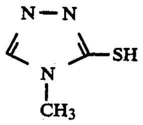
(d-69)
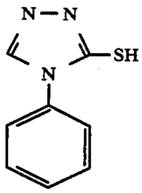
(d-70)
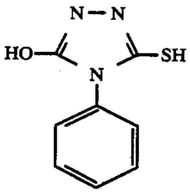
(d-71)
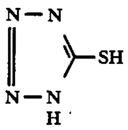
(d-72)
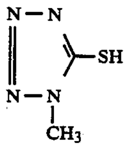
(d-73)
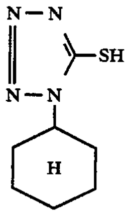
(d-74)
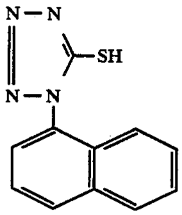
(d-75)
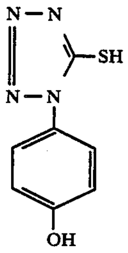
(d-76)
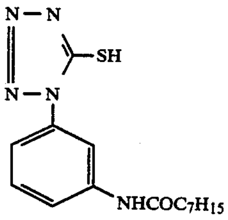
(d-77)
Silver salts of the compounds represented by formulae (I), (II), and (III) can be obtained by dissolving these compounds in a solvent, such as water, methanol, etc., and adding a silver nitrate aqueous solution thereto to effect reation. The silver salts may be used as dispersed in a binder, such as gelatin. The silver salts may also be prepared according to a process for preparing silver halide emulsions, in which silver salt formation is conducted in a protective polymer, such as gelatin, followed by precipitation and washing with water.

The silver salt as the component (c) is used in an amount of not more than 100 mols, preferably from 0.01 to 10 mols, and more preferably from 0.1 to 1 mol, per mol of the light-sensitive silver halide as the component (b).

The silver salt as the component (d) is used in an amount of from 0.001 to 50 mol%, preferably from 0.01 to 10 mol%, and more preferably from 0.01 to 5 mol%, based on the total amount of the light-sensitive silver halide as the component (b) and the silver salt of the compound of formula (I) and/or as the component (c).

The most suitable amounts of these silver salts can be selected from the above-recited ranges according to the specific compounds used.

The silver salts as the components (c) and (d) may be incorporated into different layers, but are preferably incorporated into the same layer. Further, these silver salts may be added to layers other than the light-sensitive layer. However, since the components (c) and (d) are considered to participate in a redox reaction upon heat development using a latent image of the silver halide, component (b), as a catalyst, it is desirable for the components (c) and (d) to be present in contact with or close to the light-sensitive silver halide as the component (b). Therefore, these silver salts are usually incorporated into a light-sensitive layer.

In addition to the silver salts of the compounds represented by formulae (I), (II), and (III), other known organic silver salts may be employed in the present invention. Such organic silver salts to be used in combination include those disclosed in Japanese Patent Application (OPI) No. 58543/83 (U.S. Pat. No. 4,500,626).

The silver halide which can be used as the component (b) may be any of silver chloride, silver bromide, silver iodide, silver chlorobromide, silver chloroiodide, silver iodobromide, the silver chloroiodobromide.

A halogen composition in the silver halide grains may be uniform or the silver halide grains may have a multilayer structure in which the composition is different between a surface portion and an inner portion (see Japanese Patent Application (OPI) Nos. 154232/82 (U.S. Pat. No. 4,444,877), 108533/83, 48755/84 (U.S. Pat. No. 4,507,386), and 52237/84, U.S. Pat. No. 4,433,048 and European Pat. No. 100,984, etc.).

Also a tabular grain silver halide emulsion containing grains having a thickness of 0.5 μm or less, a diameter of at least 0.6 μm, and an average aspect ratio of 5 or more (see U.S. Pat. Nos. 4,414,310 and 4,435,499, and West German Patent Application (OLS) No. 3,241,646A1, etc.), and a mono-dispersed emulsion having a nearly uniform distribution of grain size (see Japanese Patent Application (OPI) Nos. 178235/84 (U.S. Pat. No. 4,446,228), 100846/83 (U.S. Pat. Nos. 4,446,226 and 4,511,648), and 14829/83, PCT Application (OPI) No. 83/02338A1, and European Pat. Nos. 64,412A3 and 83,377A1, etc.) may be used in the present invention.

Two or more kinds of silver halides in which a crystal habit, a halogen composition, a grain size and/or a distribution of grain size, etc., are different from each other may be used in mixture. Further, two or more kinds of mono-dispersed emulsions having different grain size from each other may be employed in mixture to control gradation.

An average grain size of the silver halide used in the present invention is preferably from 0.001 μm to 10 μm and more preferably from 0.001 μm to 5 μm.

These silver halide emulsions can be prepared by any of an acid process, a neutral process, and an ammonia process. Further, a reaction system of soluble silver salts and soluble halogen salts may be any of a single jet process, a double jet process, and a combination thereof. In addition, a reverse mixing process in which silver halide grains are formed in the presence of an excess of silver ions, or a controlled double jet process in which the pAg in the liquid phase is kept constant, can also be utilized.

Moreover, for the purpose of increase in growth of grains, a concentration, amount and/or speed of addition of silver salts and halogen salts to be added may be raised (see Japanese Patent Application (OPI) Nos. 142329/80 and 158124/80, and U.S. Pat. No. 3,650,757, etc.).

Furthermore, silver halide grains of epitaxial junction type (see Japanese Patent Application (OPI) No. 16124/81, and U.S. Pat. No. 4,094,684, etc.) may be employed.

In the step of formation of silver halide grains which can be used in the present invention, ammonia, an organic thioether derivative as described in Japanese Patent Publication No. 11386/72, or a compound containing sulfur as described in Japanese Patent Application (OPI) No. 144319/78, etc., can be used as a solvent for silver halide.

In a process of the formation or physical ripening of silver halide grains, a cadmium salt, a zinc salt, a lead salt, or a thallium salt, etc., may be coexistent. Further, for the purpose of eliminating high-intensity reciprocity law failure or low-intensity reciprocity law failure, a water-soluble iridium salt such as iridium (III, IV) chloride, ammonium hexachloroiridiate, etc, or a water-soluble rhodium salt such as rhodium chloride, etc., can be used.

Soluble salts may be removed from the silver halide emulsion after precipitate formation or physical ripening, and a noodle washing process or a flocculation process can be used for this purpose.

While the silver halide emulsion may be employed without being subjected to after-ripening, it is usually chemically sensitized. For the chemical sensitization, a sulfur sensitization method, a reduction sensitization method, and a noble metal sensitization method, etc., which is known in the field of emulsions for conventional type photographic light-sensitive materials can be applied alone or in combination therewith. Such a chemical sensitization may be carried out in the presence of a nitrogen-containing heterocyclic compound (see Japanese Patent Application (OPI) Nos. 126526/83 and 215644/83, etc.).

The silver halide emulsion used in the present invention can be those in which a latent image is formed mainly on the surface of grains, or those in which a latent image is formed mainly in the interior of grains. Further, a direct reversal emulsion in which in internal latent image type emulsion and a nucleating agent are used in a combination may be used. Examples of the internal latent image type emulsions suitable for this purpose are described in U.S. Pat. Nos. 2,592,250 and 3,761,276, Japanese Patent Publication No. 3534/83, and Japanese Patent Application (OPI) No. 136641/82, etc. Preferred examples of the nucleating agents suitably used in the present invention are described in U.S. Pat. Nos. 3,227,552, 4,245,037, 4,225,511, 4,266,031, and 4,276,364, and West German Patent Application (OLS) No. 2,635,316, etc.

The coating amount of the light-sensitive silver halide used in the present invention is preferably in a range of from 1 mg/m$^2$ to 10 g/m$^2$, calculated based on the amount of silver.

In the present invention, the reducing agent as component (e) is incorporated into the light-sensitive material. The reducing agents which can be used in the present invention include dye providing substances having a reducing property. Further, precursors of reducing agents which do not have a reducing property themselves but exhibit a reducing property due to action of a nucleophilic reagent or heat in the process of development are also included.

Examples of the reducing agents which can be used in the present invention include an inorganic reducing agent such as sodium sulfite, sodium hydrogen sulfite, etc., a benzenesulfinic acid, a hydroxylamine, a hydrazine, a boran-amine complex, a hydroquinone, an aminophenol, a catechol, a p-phenylenediamine, a 3-pyrazolidinone, a hydroxytetronic acid, an ascorbic acid, a 4-amino-5-pyrazolone, etc. Reducing agents as described in T. H. James, *The Theory of the Photographic Process*, Fourth Edition, 1977, pp. 291 to 334 can also be employed. Further, reducing agent precursors as described in Japanese Patent Application (OPI) Nos. 138736/81 (U.S. Pat. No. 4,366,240) and 40245/82, U.S. Pat. No. 4,330,617, etc., can be employed.

Examples of more preferred reducing agents include the following compounds.

3-Pyrazolidones and precursors thereof (for example, 1-phenyl-3-pyrazolidone, 1-phenyl-4,4-dimethyl-3-pyrazolidone, 4-hydroxymethyl-4-methyl-1-phenyl-3-pyrazolidone, 1-m-tolyl-3-pyrazolidone, 1-p-tolyl-3-pyrazolidone, 1-phenyl-4-methyl-3-pyrazolidone, 1-phenyl-5-methyl-3-pyrazolidone, 1-phenyl-4,4-bis(hydroxymethyl)-3-pyrazolidone, 1,4-dimethyl-3-pyrazolidone, 4-methyl-3-pyrazolidone, 4,4-dimethyl-3-pyrazolidone, 1-(3-chlorophenyl)-4-methyl-3-pyrazolidone, 1-(4-chlorophenyl)-4-methyl-3-pyrazolidone, 1-(4-tolyl)-4-methyl-3-pyrazolidone, 1-(2-tolyl)-4-methyl-3-pyrazolidone, 1-(4-tolyl)-3-pyrazolidone, 1-(3-tolyl)-3-pyrazolidone, 1-(3-tolyl)-4,4-dimethyl-3-pyrazolidone, 1-(2-trifluoroethyl)-4,4-dimethyl-3-pyrazolidone, 5-methyl-3-pyrazolidone, 1,5-diphenyl-3-pyrazolidone, 1-phenyl-4-methyl-4-stearoyloxymethyl-3-pyrazolidone, 1-phenyl-4-methyl-4-lauroyloxymethyl-3-pyrazolidone, 1-phenyl-4,4-bis(lauroyloxymethyl)-3-pyrazolidone, 1-phenyl-2-acetyl-3-pyrazolidone, 1-phenyl-3-acetoxypyrazolidone, etc.); and hydroquinones and precursors thereof (for example, hydroquinone, toluhydroquinone, 2,6-dimethylhydroquinone, tert-butylhydroquinone, 2,5-di-tert-butylhydroquinone, tert-octylhydroquinone, 2,5-di-tert-octylhydroquinone, pentadecylhydroquinone, sodium 5-pentadecylhydroquinone-2-sulfonate, p-benzoyloxyphenol, 2-methyl-4-benzoyloxyphenol, 2-tert-butyl-4-(4-chlorobenzoyloxy)phenol, etc.).

Various combinations of reducing agents as described in U.S. Pat. No. 3,039,869 can also be used.

In the present invention, the amount of the reducing agent added is generally from 0.01 mol to 10 mols per mol of silver, and more preferably from 0.1 mol to 10 mols per mol of silver.

In the present invention, a wide variety of image-forming substances can be employed in various manners, in addition to the use of silver as an image-forming substance.

For instance, a compound which forms a diffusible dye or releases a diffusible dye in correspondence or counter-correspondence to the reaction wherein the light-sensitive silver halide is reduced to silver under a high temperature condition, that is, a dye-providing substance can be used in the present invention.

It is preferred that the diffusible dyes are generated imagewise when the light-sensitive material used in the present invention is heated after imagewise exposure or simultaneously with imagewise exposure.

The dye-providing substances are described in more detail below.

An example of the dye-providing substance which can be used in the present invention is a coupler capable of reacting with a developing agent. A method utilizing such a coupler can form a dye upon a reaction of the coupler with an oxidation product of a developing agent which is formed by an oxidation reduction reaction between the silver salt and the developing agent and is described in many literatures. Specific examples of the developing agents and the couplers are described in greater detail, for example, in T. H. James, *The Theory of the Photographic Process*, Fourth Edition, 1977, pp. 291 to 334 and pp. 354 to 361; and Shinichi Kikuchi, *Shashin Kagaku* (Photographic Chemistry), Fourth Edition, pp. 284 to 295, Kyoritsu Shuppan Co., etc.

Another example of the dye-providing substance is a dye-silver compound in which an organic silver salt is connected to a dye. Specific examples of the dye-silver compounds are described in *Research Disclosure*, RD No. 16966, pp. 54 to 58 (May, 1978), etc.

Still another example of the dye-providing substance is an azo dye used in a heat-developable silver dye-bleaching process. Specific examples of the azo dyes and the method for bleaching are described in U.S. Pat. No. 4,235,957, *Research Disclosure*, RD No. 14433, pp. 30 to 32 (April, 1976), etc.

A further example of the dye-providing substance is a leuco dye as described in U.S. Pat. Nos. 3,985,565 and 4,022,617, etc.

A still further example of the dye-providing substance is a compound having a function of imagewise releasing or diffusing a diffusible dye.

This type of compound can be represented by formula (LI)

$$(Dye-X)_n-Y \qquad (LI)$$

wherein Dye represents a dye moiety or a dye precursor moiety; X represents a simple bond or a connecting group; Y represents a group having such a property that diffusibility of the compound represented by $(Dye-X)_n-Y$ can be differentiated in correspondence or counter-correspondence to light-sensitive silver salts having a latent image distributed imagewise or a group having a property of releasing Dye in correspondence or counter-correspondence to light-sensitive silver salts having a latent image distributed imagewise, diffusibility of Dye released being different from that of the compound represented by $(Dye-X)_n-Y$; and n represents 1 or 2 and when n is 2, two Dye—X's are the same or different.

Specific examples of the dye-providing substance represented by formula (LI) are known and, for example, dye developers in which a hydroquinone type developing agent is connected to a dye component are described in U.S. Pat. Nos. 3,134,764, 3,362,819, 3,597,200, 3,544,545, and 3,482,972, etc. Further, substances capable of releasing diffusible dyes upon an intramolecular nucleophilic displacement reaction are described in Japanese Patent Application (OPI) No. 63618/76, etc., and substances capable of releasing diffusible dyes upon an intramolecular ring-opening and closing reaction of an isooxazolone ring are described in Japanese Patent Application (OPI) No. 111628/74, etc.

In any of these processes, diffusible dyes are released or diffused in portions where development did not occur. In contrast, in portions where development occurred neither release nor diffusion or dyes occur.

It is very difficult to obtain images of a high S/N ratio according to these processes, because development and release or diffusion of dyes occur in parallel. In order to eliminate this drawback, therefore, there has been provided a process in which a dye-releasing compound is previously converted to an oxidized form thereof which does not have a dye-releasing ability, the oxidized form of the compound is coexistent with a reducing agent or a precursor thereof, and after development the oxidized form of the compound is reduced with the remaining reducing agent which is not oxidized to release a diffusible dye. Specific examples of dye-providing substances which can be used in such a process are described in Japanese Patent Application (OPI) Nos. 110827/78, 130927/79, 164342/81, and 35533/78, etc.

On the other hand, substances capable of releasing diffusible dyes in portions where development occurred are also known. For example, substances capable of releasing diffusible dyes upon a reaction of couplers having diffusible dyes in the split-off groups thereof with oxidation products of developing agents are described in British Pat. No. 1,330,524, Japanese Patent Publication No. 39165/73, U.S. Pat. No. 3,443,940, etc., and substances capable of forming diffusible dyes upon a reaction of couplers having diffusion resistant groups in the split-off groups thereof with oxidation products of developing agents are described in U.S. Pat. No. 3,227,550, etc.

In these processes using color developing agents, there is a severe problem in that images are contaminated with oxidation decomposition products of the developing agents. Therefore, in order to eliminate such a problem, dye-releasing compounds which have a reducing property themselves, and thus do not need the use of developing agents, have been proposed. Typical examples of these dye-releasing compounds are described in U.S. Pat. Nos. 3,928,312, 4,053,312, 4,055,428 and 4,336,322, Japanese Patent Application (OPI) Nos. 65839/84, 69839/84, 3819/78 and 104343/76, *Research Disclosure,* RD No. 17465 (October, 1978), U.S. Pat. Nos. 3,725,062, 3,728,113, and 3,443,939, Japanese Patent Application (OPI) No. 116537/83, etc.

Any of various dye-providing substances described above can be employed in the present invention.

Specific examples of image-forming substances used in the present invention are described in the above-mentioned literatures.

Examples of the diffusible dyes include those derived from azo dyes, azomethine dyes, anthraquinone dyes, naphthoquinone dyes, styryl dyes, nitro dyes, quinoline dyes, carbonyl dyes, and phthalocyanine dyes, etc. These dyes can also be used in a form having temporarily shorter (shifted) wavelengths. Specific examples of the dye moieties in the dye-providing compounds include those described in Japanese Patent Application (OPI) No. 84236/84 (U.S. Pat. No. 4,473,631).

The dye-providing substance used in the present invention can be introduced into a layer of the light-sensitive material by known methods such as a method as described in U.S. Pat. No. 2,322,027, etc.

Further, it is possible to use a dispersion method using a polymer as described in Japanese Patent Publication No. 39853/76, Japanese Patent Application (OPI) No. 59943/76 (U.S. Pat. Nos. 4,512,969, 4,304,769, 4,247,627, 4,214,047, 4,199,363, and 4,203,716), etc. Moreover, various surface active agents can be used when the dye-providing substance is dispersed in a hydrophilic colloid. For this purpose, the surface active agents illustrated in other parts of the specification can be used.

An amount of the organic solvent having a high boiling point used in the present invention is 10 g, and preferably 5 g per g or less, per g of the dye-providing substance used or less.

In the present invention, an image-forming accelerator can be used. The image-forming accelerator has a function which accelerates the oxidation reduction reaction between a silver salt oxidizing agent and a reducing agent, a function which accelerates a reaction of forming a dye, decomposing a dye, or releasing a mobile dye from a dye-providing substance, etc. or a function which accelerates transfer of a dye from a layer of the light-sensitive material to a dye-fixing layer. From the standpoint of a physical or chemical function, they are classified into a group, for example, a base or a base precursor, a nucleophilic compound, an oil, a thermal solvent, a surface active agent, a compound having an interaction with silver or a silver ion, etc. However, such groups of substances usually show complex functions, and generally have some of the above described accelerating effects at the same time.

The details of these image-forming accelerators are described, e.g., in U.S. Patent Application Ser. No. 808,719, filed Dec. 13, 1985.

In the present invention, various kinds of development-stopping agents are used in the light-sensitive material for the purpose of obtaining a constant image irrespective of variation in a processing temperature and a processing time at the heat development.

The term "development-stopping agent" used herein means a compound which can rapidly neutralize a base or react with a base to decrease the concentration of the base in the layer when the development has appropriately proceeded, whereby the development is stopped or a compound which can interact with silver or a silver salt and inhibit further development.

Specific examples of the development-stopping agents are described in Japanese Patent Application (OPI) Nos. 108837/85, 230133/85, and 192939/85, etc.

Further, in the present invention, it is possible to use a compound which activates development simultaneously while stabilizing the image.

Preferred examples of the compounds used in the present invention are described in U.S. Pat. No. 4,500,626.

In the present invention, if desired, an image-toning agent can be incorporated into the light-sensitive material.

Specific examples of the useful compounds are described in U.S. Pat. No. 4,500,626.

The binder which can be used as component (a) in the light-sensitive material of the present invention can be employed individually or in a combination thereof. A hydrophilic binder can be used as the binder according to the present invention. The typical hydrophilic binder is a transparent of translucent hydrophilic colloid, examples of which include a natural substance, for example, protein such as gelatin, a gelatin derivative, a cellulose derivative, etc., a polysaccharide such as starch, gum arabic, etc., and a synthetic polymer compound, for example, a water-soluble polyvinyl compound such as polyvinyl pyrrolidone, acrylamide polymer, etc. Another example of the synthetic polymer compound is a dispersed vinyl compound in a latex form which is used for the purpose of increasing dimensional stability of a photographic material.

A suitable coating amount of the binder according to the present invention is 20 g or less, preferably 10 g or less, and more preferably 7 g or less, per $m^2$.

A suitable ratio of the organic solvent having a high boiling point which is dispersed in a binder together with a hydrophobic compound such as a dye-providing substance to the binder is 1 ml or less, preferably 0.5 ml or less, and more preferably 0.3 ml or less, per g of the binder.

In the light-sensitive material according to the present invention, the photographic emulsion layer and other binder layers may contain an inorganic or organic hardening agent. It is possible to use a chromium salt (e.g., chromium alum, chromium acetate, etc.) an aldehyde (e.g., formaldehyde, glyoxal, glutaraldehyde, etc.), an N-methylol compound (e.g., dimethylolurea, methylol dimethylhydantoin, etc.), a dioxane derivative (e.g., 2,3-dihydroxydioxane, etc.), an active vinyl compound (e.g., 1,3,5-triacryloylhexahydro-s-triazine, 1,3-vinylsulfonyl-2-propanol, 1,2-bis(vinylsulfonylacetamido)ethane, etc.), an active halogen compound (e.g., 2,4-dichloro-6-hydroxy-s-triazine, etc.), a mucohalogenic acid (e.g., mucochloric acid, mucophenoxychloric acid, etc.), etc., which are used individually or as a combination thereof.

A support used in the light-sensitive material and the dye-fixing material employed, if desired, according to the present invention is that which can tolerate the processing temperature. As an ordinary support, not only glass, paper, metal, or analogues thereof may be used, but also an acetyl cellulose film, a cellulose ester film, a polyvinyl acetal film, a polystyrene film, a polycarbonate film, a polyethylene terephthalate film, and a film related thereto or a plastic material may be used. Further, a paper support laminated with a polymer such as polyethylene, etc., can be used. A polyester as described in U.S. Pat. Nos. 3,634,089 and 3,725,070 are preferably used.

In case of using dye-providing substances which release imagewise mobile dyes in the present invention, the transfer of dyes from the light-sensitive layer to the dye-fixing layer can be carried out using a dye transfer assistant.

Specific examples of the dye transfer assistants are described in U.S. Pat. Nos. 4,463,079 and 4,500,626, Japanese Patent Application (OPI) No. 168439/84, etc.

When a dye-providing substance which is colored is incorporated into the light-sensitive material of the present invention, it is not so necessary to further incorporate an anti-irradiation or antihalation substance or various dyes into the light-sensitive material, but in order to improve the sharpness of images, filter dyes or absorbing substances as described in the literatures cited in U.S. Pat. No. 4,500,626, etc., can be incorporated into the light-sensitive material.

The light-sensitive material which can be used in the present invention may contain, if desired, various additives which are known to use in heat-developable light-sensitive materials, and layers other than the light-sensitive layer, for example, an antistatic layer, an electrically conductive layer, a protective layer, an interlayer, an antihalation layer, a stripping layer, etc. Various additives which can be used include those as described in *Research Disclosure,* Vol. 170, RD No. 17029 (June, 1978), for example, a plasticizer, a sharpness-improving dye, an antihalation dye, a sensitizing dye, a matting agent, a surface active agent, a fluorescent whitening agent, a color fading-preventing agent, etc.

The photographic material according to the present invention is preferably composed of a light-sensitive material which forms or releases a dye upon development by heating, and, if desired, a dye-fixing material for fixing a dye. Particularly in a system wherein images are formed by diffusion transfer of dyes, both the light-sensitive material and the dye-fixing material are essential. Typical photographic materials employed in such a system are divided broadly into two embodiments, that is an embodiment in which the light-sensitive material and the dye-fixing material are provided on two supports separately and an embodiment in which both materials are provided on the same support.

The embodiment in which the light-sensitive material and the dye-fixing material are formed on different supports is classified to two types. Specifically, one is a peel-apart type and the other is a non-peel-apart type.

In case of the former peel-apart type, a coated surface of the light-sensitive material and a coated surface of the dye-fixing material are superposed on to each other after imagewise exposure or heat development, and then after formation of transferred images the light-sensitive material is rapidly peeled apart from the dye-fixing material. A support for the dye-fixing material is selected from an opaque support and a transparent support depending on the fact that whether the final image is a reflective type or a transmitting type. Further, a white reflective layer may be provided on the support, if desired.

In case of the latter non-peel-apart type, it is necessary that a white reflective layer is present between a light-sensitive layer of the light-sensitive material and a dye-fixing layer of the dye-fixing material. The white reflective layer can be provided in either the light-sensitive material or the dye-fixing material. In this case, a support of the dye-fixing material is requested to be a transparent support.

One representative example of the embodiment in which the light-sensitive material and the dye-fixing material are provided on the same support is a type in which the light-sensitive material is not necessary to peel apart from the image-receiving material after the formation of transferred images. In such a case, on a transparent or opaque support a light-sensitive layer, a dye-fixing layer, and a white reflective layer are superposed. Examples of preferred embodiments of the layer structure include transparent or opaque support/light-sensitive layer/white reflective layer/dye-fixing layer, or transparent support/dye-fixing layer/white reflective layer/light-sensitive layer, etc.

Another typical example of the embodiment in which the light-sensitive material and the dye-fixing material are provided on the same support is a type in which a part or all of the light-sensitive material is peeled apart from the dye-fixing material and a stripping layer is provided on an appropriate position of the material as described, for example, in Japanese Patent Application (OPI) No. 67840/81, Canadian Pat. No. 674,082, U.S. Pat. No. 3,730,718, etc.

The light-sensitive material or the dye-fixing material may form a structure having an electrically conductive heat-generating layer suitable to use as heating means for the purpose of heat development or diffusion transfer of dyes.

In order to reproduce a wide range of color in a chromaticity diagram using three elementary colors, i.e., yellow, magenta, and cyan, it is necessary that the light-sensitive material used in the present invention contains at least three silver halide emulsion layers, each having its sensitivity in a spectral region different from the others.

Typical examples of the combination of at least three silver halide emulsion layers each having its sensitivity in a spectral region different from the others include a combination of a blue-sensitive emulsion layer, a green-sensitive emulsion layer, and a red-sensitive emulsion layer, a combination of a green-sensitive emulsion layer, a red-sensitive emulsion layer, and an infrared light-sensitive emulsion layer, a combination of a blue-sensitive emulsion layer, a green-sensitive emulsion layer, and an infrared light-sensitive emulsion layer, a combination of a blue-sensitive emulsion layer, a red-sensitive emulsion layer, and an infrared light-sensitive emulsion layer, etc. The infrared light-sensitive emulsion layer used herein means an emulsion layer having sensitivity to light in a region of 700 nm or more, and particularly in a region of 740 nm or more.

The light-sensitive material used in the present invention may have two or more light-sensitive emulsion layers which are sensitive to light of the same spectral region, but have different sensitivities, if desired.

It is necessary that each of the above-described emulsion layers and/or light-insensitive hydrophilic colloid layers adjacent to the emulsion layers contain at least one kind of a dye-providing substance capable of releasing or forming a yellow hydrophilic dye, a dye-providing substance capable of releasing or forming a magenta hydrophilic dye, and a dye-providing substance capable of releasing or forming a cyan hydrophilic dye, respectively. In other words, in each of the emulsion layers and/or light-insensitive hydrophilic colloid layers adjacent to the emulsion layers, dye-providing substances capable of releasing or forming hydrophilic dyes having different hues from each other should be incorporated, respectively. If desired, two or more kinds of dye-providing substances having the same hue may be used in mixture. In the case of using dye-providing substances which are originally colored, it is particularly advantageous that the dye-providing substances are incorporated into layers other than these emulsion layers.

The light-sensitive material used in the present invention may contain, if desired, a subsidiary layer, for example, a protective layer, an interlayer, an antistatic layer, an anti-curling layer, a stripping layer, a matting layer, etc. in addition to the above described layers.

Particularly, the protective layer usually contains an organic or inorganic matting agent for the purpose of preventing adhesion. Further, the protective layer may contain a mordant, an ultraviolet light-absorbing agent, etc. The protective layer and the interlayer may be composed of two or more layers, respectively.

Moreover, the interlayer may contain a reducing agent for preventing color mixing, an ultraviolet light-absorbing agent, a white pigment such as $TiO_2$, etc. The white pigment may be incorporated into the emulsion layer in addition to the interlayer for the purpose of increasing the sensitivity.

In order to impart the spectral sensitivity as described above to the silver halide emulsion, the silver halide emulsion may be spectrally sensitized using known sensitizing dyes so as to obtain the desired spectral sensitivity.

The dye-fixing material which can be used in the present invention comprises at least one layer containing a mordant. When the dye-fixing layer is positioned on the surface of the dye-fixing material, a protective layer can be further provided thereon, if desired.

Further, the dye transfer assistant may be sufficiently incorporated into the dye-fixing layer, if desired. The material may comprise a water-absorbing layer or a layer containing the dye transfer assistant in order to control the dye transfer assistant. These layers may be provided adjacent to the dye-fixing layer or provided through an interlayer.

The dye-fixing layer used in the present invention may be composed of two or more layers containing mordants which have mordanting powers different from each other, if desired.

The dye-fixing material used in the present invention may contain, if desired, a subsidiary layer, for example, a stripping layer, a matting layer, an anti-curling layer, etc., in addition to the above described layers.

Into one or more of the layers described above, a base and/or a base precursor for the purpose of accelerating dye transfer, a hydrophilic thermal solvent, a color fading preventing agent for preventing fading of dyes, an ultraviolet light-absorbing agent, a dispersed vinyl compound for the purpose of increasing dimensional stability, a fluorescent whitening agent, etc., may be incorporated.

The binder which can be used in the above described layers is preferably a hydrophilic binder. The typical hydrophilic binder is a transparent or translucent hydrophilic colloid, examples of which include a natural substance, for example, protein such as gelatin, a gelatin derivative, polyvinyl alcohol, a cellulose derivative, etc., a polysaccharide such as starch, gum arabic, etc., and a synthetic polymer compound, for example, dextrin, pullulan, a water-soluble polyvinyl compound such as polyvinyl alcohol, polyvinyl pyrrolidone, acrylamide polymer, etc. Among them, gelatin and polyvinyl alcohol are particularly preferred.

The dye-fixing material may have a reflective layer containing a white pigment such as titanium oxide, etc., a neutralizing layer, a neutralization-timing layer, etc., in addition to the above-described layer depending on the purposes. These layers may be provided not only in the dye-fixing material but also in the light-sensitive material. The compositions of these reflective layer, neutralizing layer, and neutralization-timing layer are described, for example, in U.S. Pat. Nos. 2,983,606, 3,362,819, 3,362,821, and 3,415,644, Canadian Pat. No. 928,559, etc.

It is advantageous that the dye-fixing material according to the present invention contains a transfer assistant described below. The transfer assistant may be incorporated into the above-described dye-fixing layer or a different layer.

In the present invention, a transparent or opaque heat-generating element is provided on a support in the case of adopting current heating as means for development, and can be prepared utilizing heretofore known techniques with respect to a resistance heat generator.

The image-receiving layer used in the present invention includes a dye-fixing layer which can be used in heat-developable color light-sensitive materials. A mordant to be used can be selected appropriately from mordants conventionally used. Among them, polymer mordants are particularly preferred. The polymer mordants include polymers containing tertiary amino groups, polymers containing nitrogen-containing heterocyclic moieties, and polymers containing quaternary cationic groups thereof, etc.

Specific examples of these polymer mordants are described in the literatures cited in U.S. Pat. No. 4,500,626, Japanese Patent Application (OPI) Nos. 60643/85, 118834/85, 119557/85, 122940/85, 122941/85, 122942/85, and 235134/85, etc.

In the present invention, a protective layer, an interlayer, a subbing layer, a back layer, and other layers can be provided by preparing each coating solution and applying it to a support by means of various coating methods such as a dip-coating method, an air-knife-coating method, a curtain-coating method, or a hopper-coating method as described in U.S. Pat. No. 3,681,294 and drying in the same manner as used in the preparation of the heat-developable light-sensitive layer, by which the light-sensitive material can be prepared.

Further, if desired, two or more layers may be applied at the same time by the method as described in U.S. Pat. No. 2,761,791 and British Pat. No. 837,095.

As light sources of imagewise exposure in order to record images on the heat-developable light-sensitive material, radiant rays including visible light can be utilized. Generally, various light sources used for conventional color prints can be used, examples of which include tungsten lamps, mercury lamps, halogen lamps such as iodine lamps, xenon lamps, laser light sources, CRT light sources, fluorescent tubes, and light-emitting diodes (LED), etc.

A heating temperature in the step of heat treatment according to the present invention can be in a range from about 50° C. to about 250° C., and preferably from about 80° C. to about 180° C.

The heat treatment step includes the heat development step and the transfer step. A heating temperature in the transfer step can be in a range from the temperature in the heat development step to room temperature. It is preferred to use a temperature up to about 10° C. lower than the temperature in the heat development step.

The dye transfer assistant (for example, water) can accelerate the transfer of images between the light-sensitive layer of heat-developable light-sensitive material and the dye-fixing layer of dye-fixing material. Also, the dye transfer assistant may be previously applied to either one of the light-sensitive layer and the dye-fixing layer or both of them and then the both layers may be superposed.

Further, a method for simultaneously or continuously carrying out the development and transfer upon heating in the presence of a small amount of a solvent (especially water), as described in detail in Japanese Patent Application (OPI) No. 218443/84, is also useful in the present invention. In this method, the heating temperature is preferably from 50° C. to the boiling point of the solvent used. For example, when water is used as the solvent, the heating temperature is preferably from 50° C. to 100° C.

In the embodiment that water is used as the solvent, an amount of water which is used is at least 0.1 time the weight of the total coating in the light-sensitive element and dye-fixing element, preferably from 0.1 time the weight of said total coating to the amount of water corresponding to the maximum swelling volume of said total coating, and more preferably from 0.1 time the weight of said total coating to an amount obtained by subtracting the weight of said total coating from the weight of water corresponding to the maximum swelling volume of said total coating.

The state of the coating at the swelling is unstable and there is a fear to cause local bleeding depending upon the condition. Thus it is preferred that the amount of water is controlled to be one corresponding to the maximum swelling volume of the total coating in the light-sensitive element and dye-fixing element or less.

As heating means, heating by passing through between heat plates or bringing into contact with a heat plate (for example, Japanese Patent Application (OPI) No. 62635/75), heating by bringing into contact with a rotating heat drum or heat roller (for example, Japanese Patent Publication No. 10791/68), heating by passing through in hot air (for example, Japanese Patent Application (OPI) No. 32737/78), heating by passing through in an inert liquid maintaining at a constant temperature, heating by passing through along a heat generator using a roller, a belt, or a guiding material (for example, Japanese Patent Publication No. 2546/69), etc. can be used. Further, a layer of an electrically conductive material such as graphite, carbon black, metal, etc. is superposed on the dye-fixing material and the dye-fixing material is directly heated by turning on an electric current in the electrically conductive layer.

A pressure applied for superposing the heat-developable light-sensitive material and the dye-fixing material can be varied depending on various embodiments and materials to be employed. However, a range of from 0.1 $kg/cm^2$ to 100 $kg/cm^2$, and preferably from 1 $kg/cm^2$ to 50 $kg/cm^2$, is suitable, as described, for example, in Japanese Patent Application (OPI) No. 180547/84.

As means for applying pressure to the heat-developable light-sensitive material and the dye-fixing material, various methods, for example, a method in which these materials are passed through a pair of rollers, a method in which these materials are pressed using a plate of good flatness, etc., can be employed. Further, the rollers or plate used for applying the pressure may be heated in a range from room temperature to the temperature in the heat development step.

The present invention is now illustrated in greater detail with reference to the following examples, but it should be understood that the present invention is not limited thereto. In these examples, all the percents are by weight unless otherwise indicated.

EXAMPLE 1

Preparation of Silver Halide Emulsion:

In 3,000 ml of water were dissolved 40 g of gelatin and 26 g of potassium bromide, and the resulting solution was maintained at 50° C. while stirring. A solution of 34 g of silver nitrate in 200 ml of water was added to the above-prepared solution over a period of 10 minutes. A solution of 3.3 g of potassium iodide in 100 ml of water was then added thereto over a period of 2 minutes. The excessive salts were precipitated by pH adjustment and removed. The emulsion was then adjusted to a pH of 6.0 to obtain 400 g of a silver iodobromide emulsion.

Preparation of Gelatin Dispersion of Dye-Providing Substance:

Five grams of Dye-Providing Substance (1) of the following formula, 0.5 g of sodium succinic acid-2-ethylhexyl ester sulfate as a surface active agent, and 5 g of tricresyl phosphate were weighed and dissolved in 30 ml of ethyl acetate while heating at 60° C. The solution was mixed with 100 g of a 10% gelatin solution with stirring, followd by dispersion in a homogenizer at 10,000 rpm for 10 minutes. The resulting dispersion was designated as the Dye-Providing Substance Dispersion.

Dye-Donor (1):

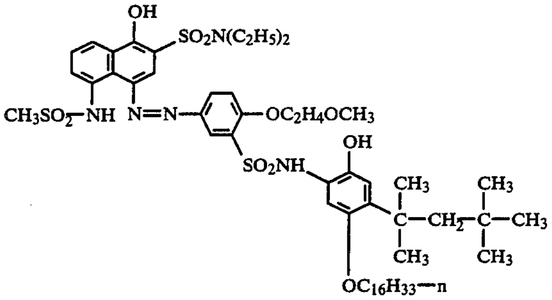

Preparation of Dispersion of Silver Salt of Compound of Formula (I):

In 3,000 ml of water were dissolved 28 g of gelatin and 13.2 g of Compound (c-1), benzotriazole, and the solution was kept at 40° C. under stirring. A solution of 17 g of silver nitrate in 100 ml of water was added thereto over 2 minutes. The excessive salts were precipitated by pH adjustment and removed. The dispersion was adjusted to a pH of 6.0 to obtain 400 g of a dispersion of a silver salt of Compound (c-1).

Preparation of Dispersion of Silver Salt of Compound of Formula (III):

In 100 ml of methanol was dissolved 1.5 g of Compound (d-1), mercaptoimidazole, and 3.4 ml of a 50 wt% silver nitrate aqueous solution was added thereto in small portions while stirring. The formed silver mercaptoimidazole was collected by filtration, washed twice with 100 ml of methanol-water and dried. A 2 g portion of the product was dispersed in 100 g of a 1% gelatin solution in a colloid mill.

Preparation of Light-Sensitive Element:

| | | |
|---|---|---|
| (i) | Silver iodobromide emulsion | 10 g |
| (ii) | Dispersion of Dye-Providing Substance (1) | 35 g |
| (iii) | 5% Aqueous solution of a compound of formula 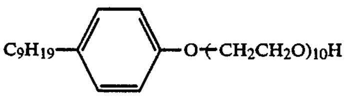 | 10 ml |
| (iv) | 10% Aqueous solution of a compound of formula $H_2NSO_2N(CH_3)_2$ | 8 ml |
| (v) | Dispersion of silver salt of | 20 g |

-continued

| | | |
|---|---|---|
| | Compound (c-1) | |
| (vi) | Solution of 1.6 g of a base precurser and guanidine trichloroacetate in 16 ml of ethanol | 4.5 ml |
| (vii) | Dispersion of a silver salt of Compound (d-1) | 1.8 g |
| (viii) | Water | 150 ml |

The above components (i) to (viii) were mixed and dissolved under heating, and the resulting coating composition was coated on a 180 μm thick polyethylene terephthalate film to a wet thickness of 33 μm and dried. Further, a protective layer having the following composition was coated thereon to a wet thickness of 30 μm, followed by drying. The resulting sample was designated as Light-Sensitive Element A.

Composition of Protective Layer:

| | |
|---|---|
| (a) 10% Aqueous gelatin solution | 30 ml |
| (b) Water | 70 ml |

Light-Sensitive Element B was produced in the same manner as for Light-Sensitive Element A except for excluding the dispersion of a silver salt of Compound (d-1) from the coating composition.

Light-Sensitive Element B' was produced in the same manner as for Light-Sensitive Element A except for excluding the dispersion of a silver salt of Compound (c-1) and the dispersion of a silver salt of Compound (d-1) from the coating composition and changing the amount of water to 170 ml.

Preparation of Dye-Fixing Element:

A uniform mixture of 0.75 g of Gelatin Hardener H-1, 0.25 g of Gelatin Hardener H-2, 160 ml of water, and 100 g of 10% lime-processed gelatin was uniformly coated on a paper support laminated with polyethylene having dispersed therein titanium dioxide to a wet thickness of 60 μm, following by drying.

Gelatin Hardener H-1:

$CH_2{=}CHSO_2CH_2CONHCH_2CH_2NHCOCH_2.SO_2CH{=}CH_2$

Gelatin Hardener H-2:

$CH_2{=}CHSO_2CH_2CONHCH_2.CH_2CH_2NHCOCH_2SO_2CH{=}CH_2$

In 200 ml of water was dissolved 15 g of a polymer having the following structure (the numbers represent mol%), and the solution was uniformly mixed with 100 g of 10% lime-processed gelatin. The mixture was uniformly coated on the above-obtained coating to a wet thickness of 85 μm, followed by drying to prepare a dye-fixing element.

Polymer:

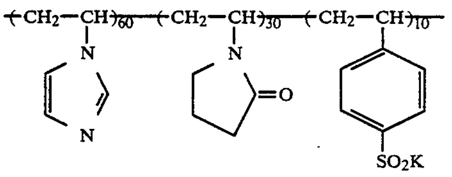

Each of Light-Sensitive Elements A, B, and B' was imagewise exposed to light emitted from a tungsten lamp (2,000 lux) to 10 seconds and uniformly heated on a heat block heated at 130° C. or 135° C. for 30 seconds or 40 seconds.

The above-prepared dye-fixing element was dipped in water and then brought into contact with the heated light-sensitive element with the coating layers of both elements facing to each other. After heating on a heat block at 80° C. for 6 seconds, the dye-fixing element was peeled apart from the light-sensitive element to thereby obtain a negative magenta dye image on the dye-fixing element. The maximum density ($D_{max}$) and the minimum density ($D_{min}$) of the negative image were determined using a Macbeth reflection densitometer (RD-519), and the results obtained are shown in Table 1.

TABLE 1

| | 130° C., 30 sec. | | 130° C., 40 sec. | | 135° C., 30 sec. | |
|---|---|---|---|---|---|---|
| Sample | $D_{max}$ | $D_{min}$ | $D_{max}$ | $D_{min}$ | $D_{max}$ | $D_{min}$ |
| A (Invention) | 2.03 | 0.17 | 2.08 | 0.21 | 2.05 | 0.20 |
| B (Comparison) | 1.79 | 0.17 | 1.98 | 0.35 | 2.00 | 0.29 |
| B' (Comparison) | 0.25 | 0.23 | 0.38 | 0.34 | 0.33 | 0.30 |

It can be seen from the above results that Sample A containing the silver salt of the compound of formula (I) as the component (c) and the silver salt of the compound of formula (III) as the component (d) in accordance with the present invention provides clear dye images having high maximum densities and low minimum densities by rapid development even with varying development time and temperatures as compared with Sample B (comparison) containing no component (c) or Sample B' (comparison) containing neither component (c) nor component (d).

EXAMPLE 2

Samples C to G were prepared and processed in the same manner as for Light-Sensitive Element A in Example 1 except for using silver salts of compounds shown in Table 2 below in place of the silver salt of Compound (d-1). The results obtained are shown in Table 2.

TABLE 2

| | Silver | Silver | 130° C., 30 sec. | | 130° C., 40 sec. | | 135° C., 30 sec. | |
|---|---|---|---|---|---|---|---|---|
| Sample | Salt | Salt | $D_{max}$ | $D_{min}$ | $D_{max}$ | $D_{min}$ | $D_{max}$ | $D_{min}$ |
| C | (c-1) | (d-5) | 2.05 | 0.17 | 2.11 | 0.19 | 2.13 | 0.20 |
| D | " | (d-33) | 1.98 | 0.14 | 2.05 | 0.17 | 2.02 | 0.16 |
| E | " | (d-54) | 2.05 | 0.15 | 2.08 | 0.20 | 2.10 | 0.18 |
| F | " | (d-64) | 2.02 | 0.20 | 2.10 | 0.25 | 2.09 | 0.23 |
| G | " | (d-63) | 2.09 | 0.18 | 2.13 | 0.20 | 2.14 | 0.21 |

The above results prove that the light-sensitive elements in accordance with the present invention exhibit stable developability as having high maximum densities and low minimum densities with little scatter even when subjected variations in development time and temperature in rapid development.

EXAMPLE 3

A multilayer color light-sensitive element was produced as follows.

Five grams of Yellow Dye-Providing Substance (2) having the following formula, 0.5 g of sodium succinic acid 2-ethylhexyl ester sulfonate as a surface active agent, and 10 g of triisononyl phosphate were weighed and dissolved in 30 ml of ethyl acetate under heating at about 60° C. to prepare a uniform solution. The resulting solution was mixed with 100 g of a 10% solution of lime-processed gelatin by stirring, and the mixture was dispersed in a homogenizer at 10,000 rpm for 10 minutes. The resulting dispersion was designated as Yellow Dye-Providing Substance Dispersion.

Magenta Dye-Proving Substance Dispersion was prepared in the same manner as described above except for using Dye-Providing Substance (1) as used in Example 1 in place of Dye-Providing Substance (2).

Cyan Dye-Providing Substance Dispersion was prepared in the same manner as for Yellow Dye-Providing Substance Dispersion except for using Cyan Dye-Providing Substance (3) having the following formula in place of Dye-Providing Substance (2).

Yellow Dye-Providing Substance (2):

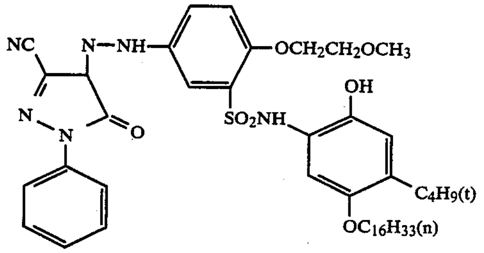

Cyan Dye-Providing Substance (3):

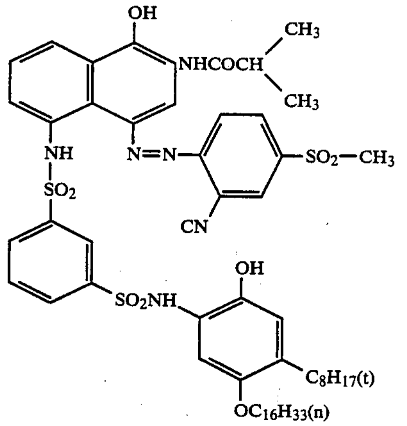

A multilayer color light-sensitive element was produced by coating a support with the following first to sixth layers in the order listed. The resulting sample was designated as Light-Sensitive Element H.

| | |
|---|---|
| First Layer (Red-Sensitive Emulsion Layer) | |
| Silver iodobromide emulsion*1 | 300 300 2 |

-continued

| | |
|---|---|
| Benzenesulfonamide | 180 $mg/m^2$ |
| Sensitizing Dye (D-2) | $8 \times 10^{-7}$ $mol/m^2$ |
| Base precursor*[2] | 440 $mg/m^2$ |
| Dispersion of silver salt of Compound (c-1) | 150 mg-$Ag/m^2$ |
| Dispersion of silver salt of Compound (d-1) | 4 mg-$Ag/m^2$ |
| Cyan Dye-Providing Substance (3) | 300 $mg/m^2$ |
| Gelatin | 1000 $mg/m^2$ |
| High boiling solvent*[3] | 600 $mg/m^2$ |
| Surface active agent*[4] | 100 $mg/m^2$ |
| Second Layer (Interlayer) | |
| Gelatin | 1000 $mg/m^2$ |
| Base precursor*[2] | 600 $mg/m^2$ |
| Third Layer (Green-Sensitive Emulsion Layer) | |
| Silver iodobromide emulsion*[1] | 300 mg-$Ag/m^2$ |
| Dimethylsulfamide | 180 $mg/m^2$ |
| Sensitizing Dye (D-1) | $10^{-6}$ $mol/m^2$ |
| Base precursor*[2] | 440 $mg/m^2$ |
| Dispersion of silver salt of Compound (c-1) | 150 mg-$Ag/m^2$ |
| Dispersion of silver salt of Compound (d-6) | 4 mg-$Ag/m^2$ |
| Magenta Dye-Providing Substance (1) | 400 $mg/m^2$ |
| Gelatin | 1000 $mg/m^2$ |
| High boiling solvent*[3] | 800 $mg/m^2$ |
| Surface active agent*[4] | 100 $mg/m^2$ |
| Fourth Layer (Interlayer) | |
| Gelatin | 1200 $mg/m^2$ |
| Base precursor*[2] | 600 $mg/m^2$ |
| Fifth Layer (Blue-Sensitive Emulsion Layer) | |
| Silver iodobromide emulsion*[1] | 300 mg-$Ag/m^2$ |
| Dispersion of silver salt of Compound (c-1) | 150 mg-$Ag/m^2$ |
| Dimethylsulfamide | 180 $mg/m^2$ |
| Base precursor*[2] | 440 $mg/m^2$ |
| Dispersion of a silver salt of Compound (d-1) | 4.5 mg-$Ag/m^2$ |
| Yellow Dye-Providing Substance (2) | 400 $mg/m^2$ |
| Gelatin | 1000 $mg/m^2$ |
| High boiling solvent*[3] | 800 $mg/m^2$ |
| Surface active agent*[4] | 100 $mg/m^2$ |
| Sixth Layer | |
| Gelatin | 1000 $mg/m^2$ |
| Base precursor*[2] | 600 $mg/m^2$ |

(Note)

*[1]The same as prepared in Example 1; iodide content is 10 mol %.

*[2]Guanidine 4-methylsulfonylphenylsulfonylacetate

*[3]$(isoC_9H_{19}O)_3P{=}O$

*[4]

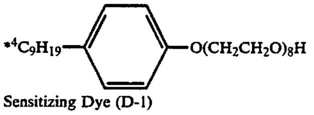

Sensitizing Dye (D-1)

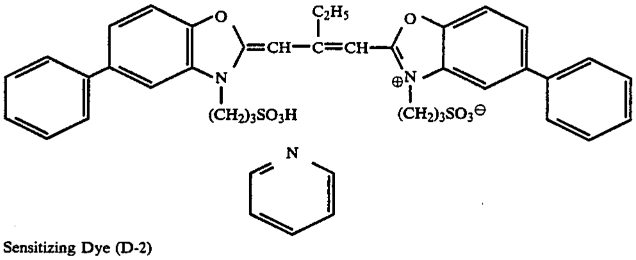

Sensitizing Dye (D-2)

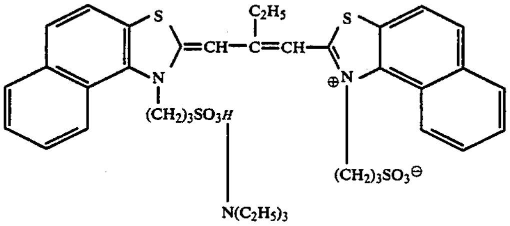

For comparison, Light-Sensitive Element I was produced in the same manner as described above except for Each of Light-Sensitive Elements H and I as prepared above was exposed to light emitted from a tungsten lamp (2,000 lux) for 10 seconds through separation filters blue (B), green (G), and red (R) having continuously changing densities. The exposed light-sensitive element was processed in the same manner as described in Example 1, except for changing the development conditions as shown in Table 3 below. The results obtained are shown in Table 3.

TABLE 3

| Sample | Separation Filter | 140° C., 30 sec. $D_{max}$ | 140° C., 30 sec. $D_{min}$ | 140° C., 35 sec. $D_{max}$ | 140° C., 35 sec. $D_{min}$ | 143° C., 30 sec. $D_{max}$ | 143° C., 30 sec. $D_{min}$ |
|---|---|---|---|---|---|---|---|
| H | B | 2.05 | 0.20 | 2.10 | 0.23 | 2.12 | 0.24 |
| (Invention) | G | 2.51 | 0.21 | 2.60 | 0.25 | 2.63 | 0.25 |
| | R | 2.13 | 0.16 | 2.21 | 0.20 | 2.23 | 0.21 |
| I | B | 1.81 | 0.23 | 1.99 | 0.36 | 2.01 | 0.38 |
| (Comparison) | G | 1.99 | 0.24 | 2.39 | 0.33 | 2.41 | 0.35 |
| | R | 1.87 | 0.21 | 2.02 | 0.29 | 2.05 | 0.28 |

As can be seen from the results of Table 3, the light-sensitive element according to the present invention exhibits stable developability showing high temperature compensation and time compensation effects and provides clear dye images having high $D_{max}$ and low $D_{min}$.

EXAMPLE 4

Light-Sensitive Element J was produced by coating a support with the first to sixth layers in accordance with the layer structure hereinafter described. The silver halide emulsions used in the first, third, and fifth layers were prepared as follows.

Preparation of Emulsion for First Layer:

Twenty grams of gelatin and 3 g of sodium chloride were dissolved in 1,000 ml of water, and the solution was kept at 75° C. while stirring well. To this gelatin solution were added simultaneously 600 ml of an aqueous solution containing sodium chloride and potassium bromide and 600 ml of an aqueous solution containing 0.59 mol of silver nitrate at the same flow rate over a period of 40 minutes. There was obtained a mono-dispersed emulsion of cubic silver chlorobromide containing 80 mol% of bromide and having a mean grain size of 0.35 μm.

After washing with water and desalting, 5 mg of sodium thiosulfate and 20 mg of 4-hydroxy-6-methyl-1,3,3a,7-tetrazaindene were added thereto to effect chemical sensitization at 60° C. The yield of the emulsion was 600 g.

Preparation of Emulsion for Third Layer:

A mono-dispersed emulsion of cubic silver chlorobromide (bromine content: 80 mol%; mean grain size: 0.35 μm) having adsorbed thereon a dye was prepared in the same manner as described for the emulsion for the first layer except that Dye Solution (I) having the following composition was added simultaneously with the potassium bromide aqueous solution and the silver nitrate aqueous solution at equal flow rates over 40 minutes. The yield of the emulsion was 600 g.

| Dye Solution (I) | |
|---|---|
| 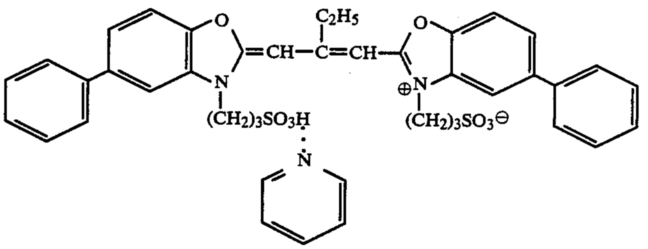 | 160 mg |
| Methanol | 400 ml |

Preparation of Emulsion for Fifth Layer:

In 1,000 ml of water were dissolved 20 g of gelatin and 10 ml of 25% ammonia, and the resulting gelatin solution was kept at 50° C. under stirring well. To the solution were added simultaneously 1,000 ml of an aqueous solution containing potassium iodide and potassium bromide and 1,000 ml of an aqueous solution containing 1 mol of silver nitrate while maintaining the pAg constant. There was obtained a mono-dispersed emulsion of octahedral silver bromoiodide containing 5 mol% of iodide and having a mean grain size of 0.5 μm.

After washing with water and desalting, 5 mg of chloroauric acid tetrahydrate and 2 mg of sodium thiosulfate were added to the emulsion to effect gold-sulfur sensitization at 60° C. The yield of the emulsion was 1 kg.

Dispersions of silver salts of the compounds of formulae (I) and (II) used in the sample preparation were prepared in the same manner as in Example 1.

| | |
|---|---|
| First Layer (Red-Sensitive Emulsion Layer): | |
| Silver chlorobromide emulsion | 200 mg-Ag/$m^2$ |
| Benzenesulfonamide | 140 mg/$m^2$ |
| Sensitizing Dye*1 | $8 \times 10^{-7}$ mol/$m^2$ |
| Dispersion of silver salt of Compound (c-1) | 230 mg-Ag/$m^2$ |
| Base precursor (A)*2 | 150 mg/$m^2$ |
| Dispersion of silver salt of Compound (d-9) | 5 mg-Ag/$m^2$ |
| Cyan Dye-Providing Substance (3) | 300 mg/$m^2$ |
| Gelatin | 850 mg/$m^2$ |
| High boiling solvent*3 | 540 mg/$m^2$ |
| Surface active agent*4 | 60 mg/$m^2$ |
| Second Layer (Interlayer): | |
| Gelatin | 1000 mg/$m^2$ |
| Base precursor*2 | 160 mg/$m^2$ |
| Third Layer (Green-Sensitive Emulsion Layer): | |
| Silver chlorobromide emulsion | 200 mg-Ag/$m^2$ |
| Dimethylsulfamide | 140 mg/$m^2$ |
| Dispersion of silver salt of Compound (c-1) | 100 mg-Ag/$m^2$ |
| Base precursor (A)*2 | 140 mg/$m^2$ |
| Magenta Dye-Providing Substance (1) | 330 mg/$m^2$ |
| Gelatin | 860 mg/$m^2$ |
| Dispersion of silver salt of Compound (d-9) | 3 mg-Ag/$m^2$ |
| High boiling solvent*3 | 430 mg/$m^2$ |
| Surface active agent*4 | 60 mg/$m^2$ |
| Fourth Layer (Interlayer): | |
| Gelatin | 700 mg/$m^2$ |
| Base precursor (A)*2 | 150 mg/$m^2$ |
| Fifth Layer (Blue-Sensitive Emulsion Layer): | |
| Silver iodobromide emulsion | 500 mg-Ag/$m^2$ |
| Dimethylsulfamide | 160 mg/$m^2$ |

-continued

| | |
|---|---|
| Base precursor (A)*2 | 180 mg/m$^2$ |
| Dispersion of silver salt of Compound (c-1) | 300 mg-Ag/m$^2$ |
| Yellow Dye-Providing Substance (2) | 400 mg/m$^2$ |
| Gelatin | 1200 mg/m$^2$ |
| Dispersion of silver salt of Compound (d-9) | 8 mg-Ag/m$^2$ |
| High boiling solvent*3 | 700 mg/m$^2$ |
| Surface active agent*4 | 70 mg/m$^2$ |
| Sixth layer: | |
| Gelatin | 740 mg/m$^2$ |
| Base precursor (A)*2 | 160 mg/m$^2$ |

(Note)

*1 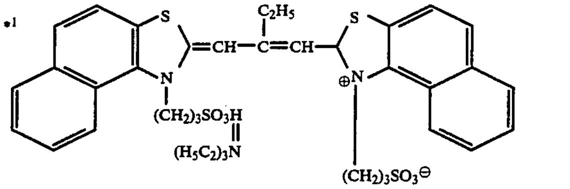

*2 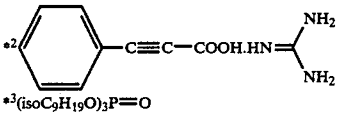

*3 $(isoC_9H_{19}O)_3P{=}O$

*4 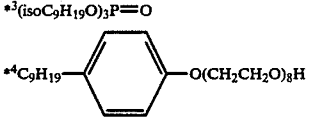

For comparison, Light-Sensitive Element K was produced in the same manner as described above except for excluding the dispersion of the silver salt of the compound of formula (II).

Preparation of Dye-Fixing Element:

In 200 ml of water was dissolved 12 g of lime-processed gelatin, and 16 ml of a 0.5M aqueous solution of zinc acetate was uniformly admixed therewith. The resulting coating composition was uniformly coated on a 100 μm thick white film support comprising polyethylene terephthalate containing titanium dioxide to a wet thickness of 85 μm, followed by drying. Then, a coating composition having the following formulation was uniformly coated thereon to a wet thickness of 90 μm and dried to obtain a dye-fixing element.

Formulation of Coating Composition:

| | |
|---|---|
| 10% Aqueous solution of polyvinyl alcohol (degree of polymerization: 2,000) | 120 g |
| Urea | 20 g |
| N—Methylurea | 20 g |
| 12% Aqueous solution of poly(N—vinylimidazole) (This polymer has a viscosity of 110 CP with respect to a 14% aqueous solution thereof (20° C.).) | 80 g |
| Water | 60 ml |

Each of Light-Sensitive Elements J and K was exposed to light from a tungsten lamp (2,000 lux) for 1 second through separation filters blue (B), green (G), and red (R) having continuously changing densities. The exposed light-sensitive element was uniformly heated on a heat block heated to 140° C. for 30 seconds.

The light-sensitive element and the above-prepared dye-fixing element were brought into contact with their coatings facing to each other, passed through a pair of pressure rolls heated to 130° C. and, immediately thereafter, heated on a heat block at 120° C. for 30 seconds. Immediately after the heating, the dye-fixing element was stripped from the light-sensitive element to obtain yellow, magenta, and cyan color images correspondingly to the separation filters blue (B), green (G), and red (R), respectively, on the dye-fixing element. Each image was determined for the maximum density ($D_{max}$) and the minimum density ($D_{min}$) by the use of a Macbeth reflection densitometer (RD-519). The results obtained are shown in Table 4 below.

TABLE 4

| Separation Filter | Sample J | | Sample K | |
|---|---|---|---|---|
| | $D_{max}$ | $D_{min}$ | $D_{max}$ | $D_{min}$ |
| B | 1.80 | 0.22 | 1.80 | 0.39 |
| G | 1.98 | 0.20 | 2.05 | 0.36 |
| R | 2.00 | 0.16 | 2.10 | 0.32 |

It can be seen that Light-Sensitive Element J according to the present invention exhibits stable developability as showing high $D_{max}$ and low $D_{min}$ against variation in transfer conditions.

EXAMPLE 5

Ten grams of Dye-Providing Substance (4) of the following formula, 0.5 g of sodium succinic acid-2-ethylhexyl ester sulfonate, and 10 g of tricresyl phosphate were weighed and dissolved in 20 ml of cyclohexanone under heating at 60° C. to form a uniform solution. The resulting solution was mixed with 100 g of a 10% aqueous solution of lime-processed gelatin with stirring, and the mixture was emulsified and dispersed in a homogenizer.

Dye-Providing Substance (4):

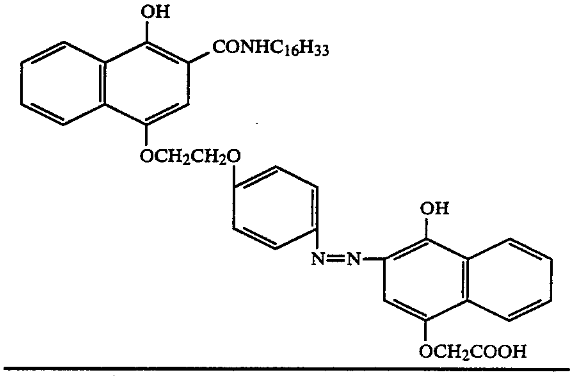

| | | |
|---|---|---|
| (i) | Silver iodobromide emulsion (the same as in Example 1) | 5.5 g |
| (ii) | 10% Gelatin aqueous solution | 0.5 g |
| (iii) | Dispersion of Dye-Providing Substance (4) as prepared above | 2.5 g |
| (iv) | 10% Ethanol solution of guanidine trichloroacetate | 1 ml |
| (v) | 10% Methanol solution of 2,6-dichloro-4-aminophenol | 0.5 ml |
| (vi) | 5% Aqueous solution of a compound of formula: 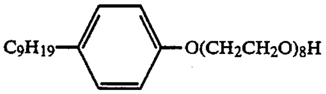 | 1 ml |
| (vii) | Dispersion of silver salt of Compound (c-1) as prepared in Example 1 | 10 g |
| (viii) | Dispersion of silver salt of Compound (d-1) as prepared | 2.5 g |

-continued

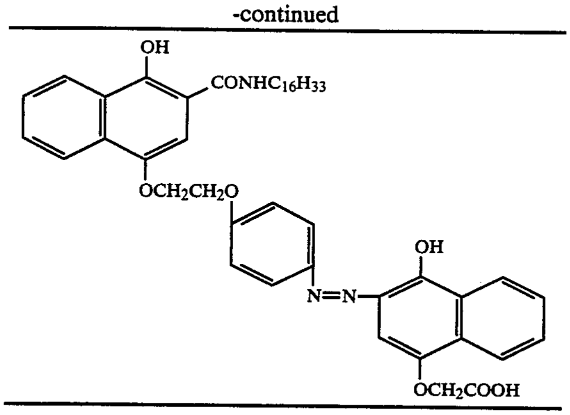

| | | |
|---|---|---|
| | in Example 1 | |
| (ix) | Water | 10 ml |

The above components (i) to (ix) were mixed and dissolved under heating, and the resulting coating composition was coated on a polyethylene terephthalate film to a wet thickness of 85 μm, followed by drying. Onto the coating film was further coated 1.5 g/m² of gelatin as a protective layer to obtain Light-Sensitive Element L.

Light-Sensitive Element L' was produced in the same manner as described above except for excluding the dispersion of the silver salt of Compound (d-1).

Each of Light-Sensitive Elements L and L' was exposed to light and processed in the same manner as in Example 1 except for changing the processing conditions as shown in Table 5 below. The results obtained are shown in Table 5.

TABLE 5

| Sample | 140° C., 30 sec. | | 140° C., 35 sec. | | 143° C., 30 sec. | |
|---|---|---|---|---|---|---|
| | $D_{max}$ | $D_{min}$ | $D_{max}$ | $D_{min}$ | $D_{max}$ | $D_{min}$ |
| L (Invention) | 1.78 | 0.23 | 1.83 | 0.26 | 1.85 | 0.25 |
| L' (Comparison) | 1.39 | 0.22 | 1.69 | 0.35 | 1.70 | 0.39 |

The above results show remarkable effects of the combined use of the components (c) and (d) according to the present invention even in light-sensitive elements containing a dye-providing substance capable of releasing a dye upon coupling reaction with an oxidation product of a developing agent.

EXAMPLE 6

A mixture comprising 5 g of Dye-Providing Substance (5) having the following formula, 4 g of an electron-donor having the following formula, 0.5 of sodium succinic acid-2-ethylhexyl ester sulfonate, and 10 g of tricresyl phosphate was dissolved in 20 ml of cyclohexanone under heating at about 60° C. The resulting solution was further worked-up in the same manner as described in Example 5 with respect to Dye-Providing Substance (4) to prepare a dispersion of a dye-releasing redox compound.

Dye-Releasing Redox Compound (5):

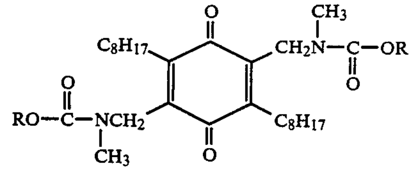

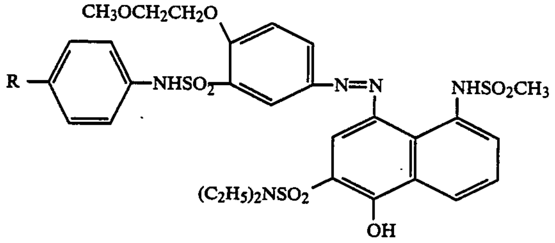

Electron-Donor

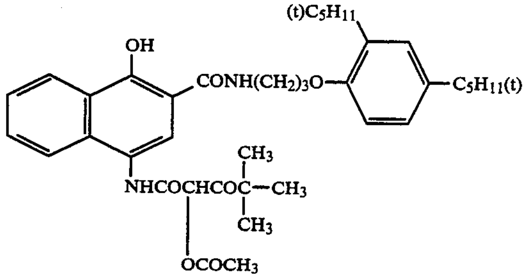

Light-Sensitive Element M was produced in the same manner as for Light-Sensitive Element L of Example 5, except for using the above-described dispersion of Dye-Releasing Redox Compound (5) in place of the dispersion of Dye-Providing Substance (4) as used in Example 5.

Light-Sensitive Element M' was produced in the same manner as described above except for exclusing the dispersion of the silver salt of Compound (d-1).

Each of Light-Sensitive Elements M and M' was exposed to light and processed in the same manner as in Example 1, but the processing conditions were changed as shown in Table 6 below. The results obtained are shown in Table 6.

TABLE 6

| Sample | 140° C., 30 sec. | | 140° C., 35 sec. | | 143° C., 30 sec. | |
|---|---|---|---|---|---|---|
| | $D_{max}$ | $D_{min}$ | $D_{max}$ | $D_{min}$ | $D_{max}$ | $D_{min}$ |
| M (Invention) | 1.46 | 0.36 | 1.40 | 0.30 | 1.41 | 0.31 |
| M' (Comparison) | 1.40 | 0.59 | 1.27 | 0.44 | 1.26 | 0.47 |

The above results prove the effectiveness of the combined use of the components (c) and (d) in accordance with the present invention even in the light-sensitive element containing a dye-releasing redox compound capable of forming an image positive to a silver image.

EXAMPLE 7

Preparation of Gelatin Dispersion of Coupler:

Five grams of 2-dodecylcarbamoyl-1-naphthol, 0.5 g of sodium succinic acid-2-ethylhexyl ester sulfonate, and 2.5 g of tricresyl phosphate were weighed and dissolved in 30 ml of ethyl acetate. The resulting solution was mixed with 100 g of a 10% gelatin solution with stirring, and the mixture was dispersed in a homogenizer at 10,000 rpm for 10 minutes.

Preparation of Light-Sensitive Element:

| | | |
|---|---|---|
| (i) | Silver iodobromide emulsion (the same as in Example 1) | 10 g |
| (ii) | Gelatin dispersion of coupler | 3.5 g |
| (iii) | Solution of 0.25 g of guanidine trichloroacetate in 2.5 ml of ethanol | whole |
| (iv) | 10% Aqueous gelatin solution | 5 g |
| (v) | Solution of 2,6-dichloro-p-aminophenol in 15 ml of water | 0.2 g |
| (vi) | Dispersion of silver salt of Compound (c-1) | 20 g |
| (vii) | Dispersion of silver salt of Compound (d-1) | 1.5 g |

A coating composition consisting of the above components (i) to (vii) was coated on a polyethylene terephthalate support to a wet thickness of 60 m and dried to produce Light-Sensitive Element N.

Light-Sensitive Element N' was produced in the same manner as described above except for excluding the dispersion of the silver salt of Compound (d-1).

Each of Light-Sensitive Element N and N' was exposed to light emitted from a tungsten lamp (2,000 lux) for 5 seconds. The exposed light-sensitive element was uniformly heated on a heat block heated at 150° C. or 153° C. for 20 seconds or 30 seconds to obtain a negative cyan dye image. Densities of the image were measured by the use of a Macbeth transmission densitometer (TD-504). The results thus-obtained are shown in Table 7 below.

TABLE 7

| | 150° C., 20 sec. | | 150° C., 30 sec. | | 153° C., 20 sec. | |
|---|---|---|---|---|---|---|
| Sample | $D_{max}$ | $D_{min}$ | $D_{max}$ | $D_{min}$ | $D_{max}$ | $D_{min}$ |
| N (Invention) | 1.87 | 0.21 | 2.09 | 0.24 | 1.99 | 0.23 |
| N' (Comparison) | 1.60 | 0.22 | 1.89 | 0.38 | 1.85 | 0.35 |

It can be seen from Table 7 that the light-sensitive element according to the present invention exerts similar effects as observed in the preceding examples even in a system using no dye-fixing element.

EXAMPLE 8

Black-and-White Light-Sensitive Element O was prepared by coating a coating composition having the following formulation on a polyethylene terephthalate support to a wet thickness of 60 m and dried.

Formulation of Coating Composition:

| | | |
|---|---|---|
| (i) | Silver iodobromide emulsion (the same as in Example 1) | 10 g |
| (ii) | Dispersion of silver salt of Compound (c-1) (the same as in Example 1) | 10 g |
| (iii) | 10% Ethanol solution of guanidine trichloroacetate | 1 ml |
| (iv) | 5% Methanol solution of a compound of formula | 2 ml |

-continued

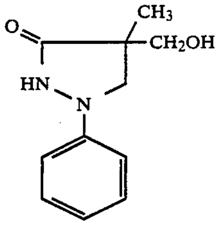

| | | |
|---|---|---|
| (v) | Dispersion of silver salt of Compound (d-1) (the same as in Example 1) | 1 g |

Light-Sensitive Element O was imagewise exposed to light of tungsten lamp (2,000 lux) for 5 seconds. When the exposed light-sensitive element was uniformly heated on a heat block heated at 130° C. or 133° C. for 30 seconds or 40 seconds, a negative brown image was obtained. Densities of the image were measured by the use of a Macbeth transmission densitometer (TD-504). The results obtained are shown in Table 8.

TABLE 8

| | 130° C., 30 sec. | | 130° C., 40 sec. | | 133° C., 30 sec. | |
|---|---|---|---|---|---|---|
| Sample | $D_{max}$ | $D_{min}$ | $D_{max}$ | $D_{min}$ | $D_{max}$ | $D_{min}$ |
| O | 0.81 | 0.18 | 0.98 | 0.19 | 0.96 | 0.20 |

As is shown in Table 8, the light-sensitive element of the present invention exerts similar effects as observed in the preceding examples even in black-and-white light-sensitive materials.

EXAMPLE 9

Preparation of Dispersion of Silver Salt of Compound (II):

Five grams of gelatin and 2.3 g of silver nitrate were dissolved in 500 ml of water, and the resulting solution was kept at 40° C. with stirring. To this solution was added a solution of 2.4 g of Compound (c-32) in 100 ml of methanol over a period of 2 minutes. The excessive salts were precipitated by pH adjustment, and the emulsion was adjusted to a pH of 6.0 to obtain 400 g of a dispersion of a silver salt of Compound (c-32).

Light-Sensitive Elements P and Q were produced in the same manner as for Light-Sensitive Elements H and I of Example 3, respectively, except that half the coverage of the dispersion of Compound (c-1) silver salt was replaced with the above-prepared dispersion of Compound (c-32) silver salt in an amount corresponding to the same silver coverage as that replaced.

Each of the light-sensitive elements was exposed to light and processed in the same manner as in Example 3, except for changing the processing conditions as shown in Table 9 below. The results obtained are also shown in Table 9.

TABLE 9

| | Separation | 150° C., 15 sec. | | 150° C., 18 sec. | | 153° C., 15 sec. | |
|---|---|---|---|---|---|---|---|
| Sample | Filter | $D_{max}$ | $D_{min}$ | $D_{max}$ | $D_{min}$ | $D_{max}$ | $D_{min}$ |
| P | B | 2.10 | 0.20 | 2.14 | 0.24 | 2.15 | 0.23 |
| (Inven- | G | 2.53 | 0.22 | 2.60 | 0.25 | 2.62 | 0.26 |
| tion) | R | 2.20 | 0.18 | 2.26 | 0.22 | 2.23 | 0.24 |
| Q | B | 1.85 | 0.22 | 2.00 | 0.40 | 1.98 | 0.38 |
| (Compar- | G | 1.98 | 0.24 | 2.36 | 0.35 | 2.48 | 0.40 |

TABLE 9-continued

| Sample | Separation Filter | 150° C., 15 sec. $D_{max}$ | 150° C., 15 sec. $D_{min}$ | 150° C., 18 sec. $D_{max}$ | 150° C., 18 sec. $D_{min}$ | 153° C., 15 sec. $D_{max}$ | 153° C., 15 sec. $D_{min}$ |
|---|---|---|---|---|---|---|---|
| ison) | R | 1.90 | 0.24 | 2.00 | 0.30 | 2.10 | 0.35 |

As can be seen from Table 9, the light-sensitive element according to the present invention exhibits stable developability showing high temperature and time compensation effects and provides a clear dye image having low $D_{min}$ and high $D_{max}$.

As described above, use of the heat-developable light-sensitive materials of the present invention makes it possible to realize development in a short time. The heat-developable light-sensitive materials of the invention exhibit developability stable with respect to variations in development temperature and time from the optimum development conditions and also provide clear color or black-and-white images having high maximum densities and low minimum densities. Further, they are excellent in working preservability.

While the invention has been described in detail and with reference to specific embodiments thereof, it will be apparent to one skilled in the art that various changes and modifications can be made therein without departing from the spirit and scope thereof.

What is claimed is:

1. A heat-developable light-sensitive material comprising a support having provided thereon at least (a) a binder;

(b) a light-sensitive silver halide;

(c) at least one silver salt of a compound represented by formula (I) or (II)

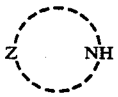

(I)

wherein Z represents a non-metallic atomic group forming a heterocyclic ring together with the nitrogen atom, $$A—C≡C—H \qquad (II)$$

wherein A represents a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group;

(d) a silver salt of a compound represented by formula (III)

$$B—S—H \qquad (III)$$

wherein B represents a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group; and (e) a reducing agent.

2. A heat-developable light-sensitive material as in claim 1, wherein the silver salt of a compound represented by formula (I) is a silver salt of a compound represented by one of formula (I-1) to (I-9)

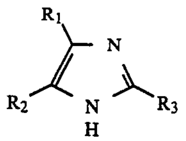

(I-1)

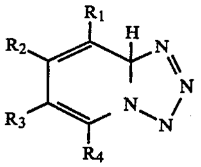

(I-2)

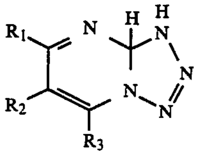

(I-3)

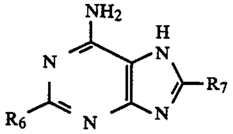

(I-4)

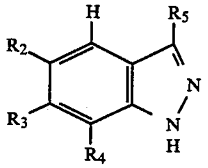

(I-5)

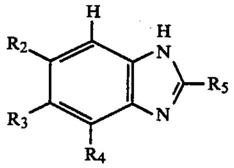

(I-6)

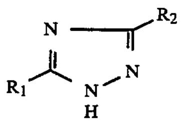

(I-7)

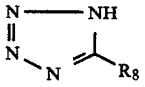

(I-8)

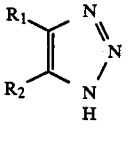

(I-9)

wherein $R_1$, $R_2$, $R_3$, and $R_4$ each represents a hydrogen atom, a substituted or unsubstituted alkyl group, a substituted or unsubstituted aralkyl group, a substituted or unsubstituted alkenyl group, a substituted or unsubstituted alkoxy group, a substituted or unsubstituted aryl group, —NRR', —COOR'', —CONRR', $—NHSO_2R$, $—SO_2NRR'$, $—NO_2$, a halogen atom, —CN, or —OH, wherein R and R' each represents a hydrogen atom, a substituted or unsubstituted alkyl group, a substituted or unsubstituted aryl group, or a substituted or unsubstituted aralkyl group; and R″ represents a substituted or unsubstituted alkyl group, a substituted or unsubstituted aryl group, or a substituted or unsubstituted aralkyl group; or $R_1$ and $R_2$ in formula (I-9) are taken together to form an aliphatic ring or an aromatic ring; $R_5$ represents a hydrogen atom, a substituted or unsubstituted alkyl group, or —S—R‴, wherein R‴ represents a hydrogen atom, an alkyl group, an aryl group, or an aralkyl group; $R_6$ represents a hydrogen atom or an alkyl group; $R_7$ represents a hydrogen atom, an alkyl group, or an aryl group; and $R_8$ represents an alkyl group, an aryl group, a benzyl group, or a pyridyl group.

3. A heat-developable light-sensitive material as in claim 2, wherein the silver salt of a compound represented by formula (I-9) is a silver salt of a compound represented by formula (I-10)

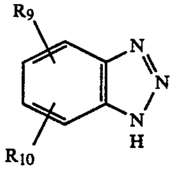
(I-10)

wherein $R_9$ and $R_{10}$ each represents a hydrogen atom a substituted or unsubstituted alkyl group, a substituted or unsubstituted aralkyl group, a substituted or unsubstituted alkenyl group, a substituted or unsubstituted alkoxy group, a substituted or unsubstituted aryl group, —NRR′, —COOR″, —CONRR′, —$NHSO_2R$, —$SO_2NRR'$, —$NO_2$, a halogen atom, —CN, or —OH, wherein R and R′ each represents a hydrogen atom, a substituted or unsubstituted alkyl group, a substituted or unsubstituted aryl group, or a substituted or unsubstituted aralkyl group; and R″ represents a substituted or unsubstituted alkyl group, a substituted or unsubstituted aryl group, or a substituted or unsubstituted aralkyl group; or $R_9$ and $R_{10}$ together form an aliphatic ring or an aromatic ring.

4. A heat-developable light-sensitive material as in claim 1, wherein A in formula (II) is a phenyl group or a substituted phenyl group.

5. A heat-developable light-sensitive material as in claim 1, wherein the silver salt of a compound represented by formula (III) is a silver salt of a compound represented by formula (III-1)

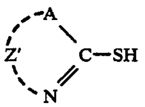
(III-1)

wherein Q represents an oxygen atom, a sulfur atom, a nitrogen atom, or —$NR_n$—, wherein $R_n$ represents a hydrogen atom, a substituted or unsubstituted alkyl group, a substituted or unsubstituted cycloalkyl group, a substituted or unsubstituted alkenyl group, a substituted or unsubstituted aryl group, or a substituted or unsubstituted aralkyl group; and Z′ represents an atomic group forming a 5- or 6-membered heterocyclic ring together with —Q—C≡N—, wherein the heterocyclic ring can have a condensed ring.

6. A heat-developable light-sensitive material as in claim 5, wherein the silver salt of a compound represented by formula (III-1) is a silver salt of a compound represented by formula (III-2)

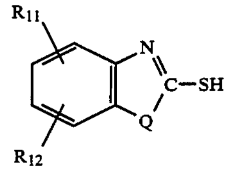
(III-2)

wherein Q is the same as defined in claim 5; and $R_{11}$ and $R_{12}$ each represents a hydrogen atom, a substituted or unsubstituted alkyl group, a substituted or unsubstituted aralkyl group, a substituted or unsubstituted alkenyl group, a substituted or unsubstituted alkoxy group, a substituted or unsubstituted aryl group, —NRR′, —COOR″, —CONRR′, —$NHSO_2R$, —$SO_2NRR'$, —$NO_2$, a halogen atom, —CN, or —OH, wherein R and R′ each represents a hydrogen atom, a substituted or unsubstituted alkyl group, a substituted or unsubstituted aryl group, or a substituted or unsubstituted aralkyl group; and R″ represents a substituted or unsubstituted alkyl group, a substituted or unsubstituted aryl group, or a substituted or unsubstituted aralkyl group; or $R_{11}$ and $R_{12}$ together form an aliphatic ring or an aromatic ring.

7. A heat-developable light-sensitive material as in claim 6, wherein Q is —NH—.

8. A heat-developable light-sensitive material as in claim 1, wherein the component (c) is present in an amount not more than 100 mols per mol of the light-sensitive silver halide as the component (b).

9. A heat-developable light-sensitive material as in claim 8, wherein the component (c) is present in an amount of from 0.01 to 10 mols per mol of the light-sensitive silver halide as the component (b).

10. A heat-developable light-sensitive material as in claim 9, wherein the component (c) is present in an amount of from 0.1 to 1 mol per mol of the light-sensitive silver halide as the component (b).

11. A heat-developable light-sensitive material as in claim 1, wherein the component (d) is present in an amount of from 0.001 to 50 mol% based on the total amount of the light-sensitive silver halide as the component (b) and the silver salt of the compound represented by formula (I) and/or (II) as the component (c).

12. A heat-developable light-sensitive material as in claim 11, wherein the component (d) is present in an amount of from 0.01 to 10 mol% based on the total amount of the light-sensitive silver halide as the component (b) and the silver salt of the compound represented by formula (I) and/or (II) as the component (c).

13. A heat-developable light-sensitive material as in claim 12, wherein the component (d) is present in an amount of from 0.01 to 5 mol% based on the total amount of the light-sensitive silver halide and as the component (b) the silver salt of the compound represented by formula (I) and/or (II) as the component (c).

14. A heat-developable light-sensitive material as in claim 1, wherein the components (c) and (d) are present in the same layer.

15. A heat-developable light-sensitive material as in claim 1, wherein the components (c) and (d) are present in a light-sensitive layer.

16. A heat-developable light-sensitive material as in claim 2, wherein $R_1$, $R_2$, $R_3$, and $R_4$ each represents a substituted or unsubstituted alkyl group having from 1 to 22 carbon atoms, a substituted or unsubstituted aralkyl group, a substituted or unsubstituted alkenyl group having from 1 to 22 carbon atoms, a substituted or unsubstituted alkoxy group having from 1 to 22 carbon atoms, a substituted or unsubstituted phenyl group, —NRR′, —COOR″, —CONRR′, —$NHSO_2R$, —$SO_2NRR'$, —$NO_2$, a halogen atom, —CN, or —OH, wherein R and R′ each represents a hydrogen atom, a substituted or unsubstituted alkyl group having from 1 to 22 carbon atoms, a substituted or unsubstituted phenyl group, or a substituted or unsubstituted aralkyl group; and R″ represents a substituted or unsubstituted alkyl group having from 1 to 22 carbon atoms, a substituted or unsubstituted phenyl group, or a substituted or unsubstituted aralkyl group; or $R_1$ and $R_2$ in formula (I-9) are taken together to form an aliphatic ring or an aromatic ring; $R_5$ represents a hydrogen atom, a substituted or unsubstituted alkyl group having from 1 to 5 carbon atoms, or —S—R‴, wherein R‴ represents a hydrogen atom, an alkyl group, an aryl group, or an aralkyl group; $R_6$ represents a hydrogen atom or an alkyl group; $R_7$ represents a hydrogen atom, an alkyl group, or an aryl group; and $R_8$ represents an alkyl group, an aryl group, a benzyl group, or a pyridyl group.

17. A heat-developable light-sensitive material comprising a support having provided thereon at least (a) a binder;

(b) a light-sensitive silver halide;

(c) at least one silver salt of a compound represented by formula (II)

$$A—C≡C—H \qquad (II)$$

wherein A represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group, or a substituted or unsubstituted heterocyclic group;

(d) a silver salt of a compound represented by formula (III)

$$B—S—H \qquad (III)$$

wherein B represents a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group; and (e) a reducing agent.

* * * * *